United States Patent
Ciccone et al.

(10) Patent No.: US 10,293,150 B2
(45) Date of Patent: May 21, 2019

(54) CONNECTOR SYSTEM FOR RELEASABLY CONNECTING FLUID CONDUITS

(71) Applicant: WilMarc Holdings, LLC, Fort Collins, CO (US)

(72) Inventors: Paul C. Ciccone, Social Circle, GA (US); William A. Coulson, Fort Collins, CO (US); Marcia Coulson, Fort Collins, CO (US)

(73) Assignee: WilMarc Holdings, LLC, Fort Collins, CO (US)

( * ) Notice: Subject to any disclaimer, the term of this patent is extended or adjusted under 35 U.S.C. 154(b) by 0 days.

(21) Appl. No.: 15/447,033

(22) Filed: Mar. 1, 2017

(65) Prior Publication Data

US 2017/0205011 A1  Jul. 20, 2017

Related U.S. Application Data

(63) Continuation of application No. 15/410,636, filed on Jan. 19, 2017, now Pat. No. 10,173,046.
(Continued)

(51) Int. Cl.
*F16L 37/34* (2006.01)
*A61M 39/10* (2006.01)
(Continued)

(52) U.S. Cl.
CPC ........ *A61M 39/1011* (2013.01); *A61M 39/22* (2013.01); *A61M 39/26* (2013.01);
(Continued)

(58) Field of Classification Search
CPC ... F16L 37/34; F16L 37/32; Y10T 137/87949; Y10T 137/87957; A61M 39/22; A61M 39/26
(Continued)

(56) References Cited

U.S. PATENT DOCUMENTS 2,218,318 A    10/1940  Pfauser
2,451,218 A    10/1948  Hengst
(Continued)

OTHER PUBLICATIONS

PCT International Patent Application No. PCT/US2017/014189; International Search Report and Written Opinion of the International Searching Authority, dated May 23, 2017, 13 pages total.
(Continued)

*Primary Examiner* — Kevin L Lee

(74) *Attorney, Agent, or Firm* — Craig R. Miles; CR Miles P.C.

(57) ABSTRACT

Disclosed herein are embodiments of a connector system for releasably connecting together tubes, for example medical tubing, and methods of making and using such a connector system, whereby the connector system includes a female coupler having a first passageway, a male coupler having a second passageway, a catch movably coupled to the female coupler, and a catch-receiving element coupled to the male coupler. The connector system further includes a release element movably coupled to the female coupler, whereby travel of the release element along or over a female coupler outer surface of the female coupler disengages the catch from the catch-receiving element to achieve a disconnected condition of the connector system. Further disclosed herein are embodiments of a connector system for releasably connecting together tubes, whereby the connector system includes at least one valve biased by a valve-biasing member disposed external to or outside of the fluid flow path.

19 Claims, 22 Drawing Sheets

Related U.S. Application Data

(60) Provisional application No. 62/299,499, filed on Feb. 24, 2016, provisional application No. 62/280,354, filed on Jan. 19, 2016.

(51) Int. Cl.
- *A61M 39/22* (2006.01)
- *F16L 37/23* (2006.01)
- *F16L 37/26* (2006.01)
- *F16L 37/32* (2006.01)
- *A61M 39/26* (2006.01)

(52) U.S. Cl.
CPC .............. *F16L 37/23* (2013.01); *F16L 37/26* (2013.01); *F16L 37/32* (2013.01); *F16L 37/34* (2013.01); *A61M 2039/1016* (2013.01); *A61M 2039/1027* (2013.01); *A61M 2039/1044* (2013.01); *A61M 2205/0205* (2013.01); *A61M 2205/581* (2013.01); *A61M 2205/582* (2013.01); *A61M 2205/583* (2013.01)

(58) Field of Classification Search
USPC .................................................. 137/614.03
See application file for complete search history.

(56) References Cited

U.S. PATENT DOCUMENTS

| | | | |
|---|---|---|---|
| 2,545,796 | A * | 3/1951 | Scheiwer ............. F16L 37/23 137/614.03 |
| 2,805,089 | A | 9/1957 | Hansen |
| 2,854,259 | A * | 9/1958 | Clark .................. F16L 37/23 137/614.03 |
| 3,291,152 | A | 12/1966 | Comer |
| 3,460,801 | A | 8/1969 | Norton |
| 3,592,231 | A | 7/1971 | Lamb |
| 3,719,194 | A | 3/1973 | Anderson et al. |
| 3,916,929 | A | 11/1975 | Brown |
| 4,220,174 | A | 9/1980 | Spitz |
| 4,436,125 | A | 3/1984 | Blenkush |
| 4,500,118 | A | 2/1985 | Blenkush |
| 4,541,457 | A | 9/1985 | Blenkush |
| 4,630,847 | A | 12/1986 | Blenkush |
| 4,703,957 | A | 11/1987 | Blenkush |
| 4,733,692 | A * | 3/1988 | Kotake et al. .......... F16L 37/23 137/614.03 |
| 4,819,692 | A * | 4/1989 | Olson et al. .......... F16L 29/04 137/614.03 |
| 4,877,145 | A | 10/1989 | Manner |
| 4,903,995 | A | 2/1990 | Blenkush et al. |
| 4,934,655 | A | 6/1990 | Blenkush et al. |
| 4,946,200 | A | 8/1990 | Blenkush et al. |
| 5,009,252 | A | 4/1991 | Faughn |
| 5,033,777 | A | 7/1991 | Blenkush |
| 5,052,725 | A | 10/1991 | Meyer et al. |
| 5,076,615 | A | 12/1991 | Sampson |
| 5,104,158 | A | 4/1992 | Meyer et al. |
| 5,165,733 | A | 11/1992 | Sampson |
| 5,178,303 | A | 1/1993 | Blenkush et al. |
| D339,417 | S | 9/1993 | Sampson et al. |
| 5,259,894 | A | 11/1993 | Sampson |
| 5,295,339 | A | 3/1994 | Manner |
| 5,316,041 | A | 5/1994 | Ramacier, Jr. et al. |
| 5,353,836 | A | 10/1994 | deCler et al. |
| 5,390,702 | A | 2/1995 | Smith, III |
| D357,307 | S | 4/1995 | Ramacier, Jr. et al. |
| 5,460,413 | A | 10/1995 | Sampson |
| 5,494,074 | A | 2/1996 | Ramacier, Jr. et al. |
| 5,529,085 | A | 6/1996 | Richards et al. |
| D372,093 | S | 7/1996 | Sampson et al. |
| D375,160 | S | 10/1996 | Sampson et al. |
| 5,564,752 | A | 10/1996 | Sampson |
| 5,639,064 | A | 6/1997 | deCler et al. |
| D384,731 | S | 10/1997 | Ramacier, Jr. et al. |
| 5,695,221 | A | 12/1997 | Sunderhaus |
| D388,876 | S | 1/1998 | Sampson |
| 5,704,106 | A | 1/1998 | Sampson et al. |
| 5,799,987 | A | 9/1998 | Sampson |
| 5,820,614 | A | 10/1998 | Erskine et al. |
| 5,826,610 | A | 10/1998 | Bodhaine |
| 5,845,943 | A | 12/1998 | Ramacier, Jr. et al. |
| 5,848,811 | A | 12/1998 | Sampson |
| 5,848,997 | A | 12/1998 | Erskine et al. |
| 5,869,803 | A | 2/1999 | Noguchi et al. |
| 5,911,403 | A | 6/1999 | deCler et al. |
| 5,937,885 | A | 8/1999 | Sampson |
| 5,938,244 | A | 8/1999 | Meyer |
| 5,975,489 | A | 11/1999 | deCler et al. |
| 6,024,124 | A | 2/2000 | Braun et al. |
| 6,082,401 | A | 7/2000 | Braun et al. |
| 6,095,191 | A | 8/2000 | Smith, III |
| 6,146,374 | A | 11/2000 | Erskine et al. |
| 6,161,578 | A | 12/2000 | Braun et al. |
| 6,206,040 | B1 | 3/2001 | Smith, III |
| 6,231,089 | B1 | 5/2001 | deCler et al. |
| 6,382,593 | B1 | 5/2002 | deCler et al. |
| 6,626,419 | B2 | 9/2003 | deCler et al. |
| 6,649,829 | B2 | 11/2003 | Garber et al. |
| 6,705,591 | B2 | 3/2004 | deCler |
| 6,848,602 | B2 | 2/2005 | deCler et al. |
| 6,871,669 | B2 | 3/2005 | Meyer et al. |
| D503,778 | S | 4/2005 | Wicks |
| 6,897,374 | B2 | 5/2005 | Garber et al. |
| 6,902,144 | B2 | 6/2005 | deCler |
| 6,916,007 | B2 | 7/2005 | deCler et al. |
| 6,962,275 | B2 | 11/2005 | deCler et al. |
| 6,978,800 | B2 | 12/2005 | deCler et al. |
| 7,080,665 | B2 | 7/2006 | Whall |
| 7,163,022 | B2 | 1/2007 | Whall |
| 7,394,375 | B2 | 7/2008 | Johnson |
| 7,434,842 | B2 | 10/2008 | Schmidt |
| 7,448,653 | B2 | 11/2008 | Jensen et al. |
| 7,469,472 | B2 | 12/2008 | deCler et al. |
| 7,488,446 | B2 | 2/2009 | Meyer et al. |
| 7,514,025 | B2 | 4/2009 | Hofmann et al. |
| 7,546,857 | B2 | 6/2009 | Chadbourne et al. |
| 7,547,047 | B2 | 6/2009 | deCler et al. |
| 7,562,906 | B2 | 7/2009 | Schmidt |
| D602,128 | S | 10/2009 | Williams et al. |
| 7,631,660 | B2 | 12/2009 | deCler et al. |
| 7,647,954 | B2 | 1/2010 | Garber et al. |
| D612,019 | S | 3/2010 | Williams et al. |
| D612,021 | S | 3/2010 | Schmidt |
| 7,695,020 | B2 | 4/2010 | Schmidt |
| 7,708,025 | B2 | 5/2010 | Johnson |
| 7,757,974 | B2 | 7/2010 | Hofmann et al. |
| 7,770,939 | B2 | 8/2010 | Jensen et al. |
| 7,806,139 | B2 | 10/2010 | Packham et al. |
| 7,828,336 | B2 | 11/2010 | Gammons |
| 7,841,357 | B2 | 11/2010 | Rankin |
| D629,894 | S | 12/2010 | Lombardi, III et al. |
| D630,320 | S | 1/2011 | Lombardi, III et al. |
| 7,875,346 | B2 | 1/2011 | Hofmann et al. |
| 7,878,553 | B2 | 2/2011 | Wicks et al. |
| D634,840 | S | 3/2011 | Lombardi, III et al. |
| D639,398 | S | 6/2011 | Wilhelm |
| 7,954,374 | B2 | 6/2011 | Rankin |
| 7,954,515 | B2 | 6/2011 | Gerst |
| D642,244 | S | 7/2011 | Wilhelm |
| D645,547 | S | 9/2011 | Lombardi et al. |
| D649,240 | S | 11/2011 | Lewis et al. |
| D649,938 | S | 12/2011 | Erickson et al. |
| D649,939 | S | 12/2011 | Erickson et al. |
| D650,478 | S | 12/2011 | Lewis |
| D652,510 | S | 1/2012 | Lombardi, III et al. |
| D652,511 | S | 1/2012 | Lombardi, III et al. |
| D654,573 | S | 2/2012 | Lombardi et al. |
| 8,113,546 | B2 | 2/2012 | Jensen et al. |
| D655,393 | S | 3/2012 | Whitaker |
| 8,162,242 | B2 | 4/2012 | Hofmann et al. |
| D663,022 | S | 7/2012 | Lombardi, III et al. |
| 8,235,426 | B2 | 8/2012 | Pisula, Jr. et al. |

(56) References Cited

U.S. PATENT DOCUMENTS

| | | | |
|---|---|---|---|
| 8,256,803 B2 * | 9/2012 | Takahashi | F16L 37/23 |
| | | | 285/276 |
| 8,388,873 B2 | 3/2013 | Hofmann et al. | |
| 8,397,756 B2 | 3/2013 | Packham et al. | |
| 8,448,994 B2 | 5/2013 | Pisula, Jr. et al. | |
| RE44,310 E | 6/2013 | Chadbourne et al. | |
| 8,491,016 B2 | 7/2013 | Williams et al. | |
| 8,596,688 B2 | 12/2013 | Pisula, Jr. et al. | |
| D698,440 S | 1/2014 | Lombardi, III et al. | |
| D699,841 S | 2/2014 | Lombardi, III et al. | |
| 8,684,035 B2 * | 4/2014 | Bernhard | E02F 3/3654 |
| | | | 137/614.03 |
| D712,537 S | 9/2014 | Lombardi et al. | |
| 8,897,756 B2 | 11/2014 | Skog et al. | |
| 8,945,091 B2 | 2/2015 | Williams et al. | |
| D724,703 S | 3/2015 | Downs | |
| 9,027,968 B2 | 5/2015 | Gerst | |
| 9,046,205 B2 | 6/2015 | Whitaker et al. | |
| 9,157,560 B2 | 10/2015 | Rehder et al. | |
| 9,266,257 B2 | 2/2016 | Hofmann et al. | |
| 9,279,530 B2 | 3/2016 | Schmidt | |
| 9,364,653 B2 | 6/2016 | Williams et al. | |
| 9,371,921 B2 | 6/2016 | Whitaker | |
| D761,395 S | 7/2016 | Plackner et al. | |
| 9,388,929 B2 | 7/2016 | Lewis et al. | |
| D762,826 S | 8/2016 | Plackner et al. | |
| 9,464,741 B2 | 10/2016 | Lewis et al. | |
| 9,498,800 B2 | 11/2016 | Hofmann et al. | |
| 9,506,590 B2 | 11/2016 | Wilhelm et al. | |
| 2001/0035220 A1 | 11/2001 | Russell | |
| 2002/0011730 A1 | 1/2002 | Stickan | |
| 2002/0014608 A1 | 2/2002 | deCler et al. | |
| 2002/0063427 A1 | 5/2002 | Schiemann et al. | |
| 2002/0074533 A1 | 6/2002 | DeCler et al. | |
| 2002/0101076 A1 | 8/2002 | Barrier | |
| 2002/0129858 A1 | 9/2002 | Meyer et al. | |
| 2002/0170731 A1 | 11/2002 | Garber et al. | |
| 2002/0190453 A1 | 12/2002 | Wilhelm et al. | |
| 2003/0062498 A1 | 4/2003 | DeCler et al. | |
| 2003/0062501 A1 | 4/2003 | DeCler | |
| 2003/0196703 A1 | 10/2003 | DeCler et al. | |
| 2004/0079423 A1 * | 4/2004 | Mikiya et al. | F16L 37/34 |
| | | | 137/614.03 |
| 2004/0130438 A1 | 7/2004 | Garber | |
| 2004/0169368 A1 | 9/2004 | Garber et al. | |
| 2004/0173769 A1 | 9/2004 | DeCler | |
| 2004/0222180 A1 | 11/2004 | Wicks et al. | |
| 2004/0232175 A1 | 11/2004 | DeCler et al. | |
| 2005/0001425 A1 | 1/2005 | DeCler et al. | |
| 2005/0012330 A1 | 1/2005 | Schmidt | |
| 2005/0057042 A1 | 3/2005 | Wicks | |
| 2005/0076964 A1 | 4/2005 | Whall | |
| 2005/0082828 A1 | 4/2005 | Wicks et al. | |
| 2005/0084410 A1 | 4/2005 | Meyer et al. | |
| 2005/0127117 A1 | 6/2005 | DeCler et al. | |
| 2005/0211934 A1 | 9/2005 | Garber et al. | |
| 2005/0237241 A1 | 10/2005 | Garber et al. | |
| 2005/0247371 A1 | 11/2005 | Chadbourne et al. | |
| 2006/0048849 A1 | 3/2006 | DeCler | |
| 2006/0076419 A1 | 4/2006 | Johnson | |
| 2006/0138704 A1 | 6/2006 | DeCler et al. | |
| 2006/0186233 A1 | 8/2006 | Holm et al. | |
| 2006/0196556 A1 | 9/2006 | Johnson | |
| 2006/0207345 A1 | 9/2006 | Rankin | |
| 2006/0231137 A1 | 10/2006 | Whall | |
| 2007/0001452 A1 | 1/2007 | Friel | |
| 2007/0025811 A1 | 2/2007 | Wilhelm | |
| 2007/0169825 A1 | 7/2007 | Packham et al. | |
| 2007/0209716 A1 | 9/2007 | Rankin | |
| 2007/0259246 A1 * | 11/2007 | Jang et al. | H01M 8/04201 |
| | | | 429/509 |
| 2008/0011785 A1 | 1/2008 | Braun et al. | |
| 2008/0061553 A1 | 3/2008 | Schmidt | |
| 2008/0067807 A1 | 3/2008 | DeCler et al. | |
| 2008/0191069 A1 | 8/2008 | Hofmann et al. | |
| 2008/0277924 A1 | 11/2008 | Jensen et al. | |
| 2009/0188575 A1 | 7/2009 | Williams et al. | |
| 2009/0256355 A1 | 10/2009 | Wicks et al. | |
| 2009/0284007 A1 | 11/2009 | Schmidt | |
| 2010/0001516 A1 | 1/2010 | Pisula, Jr. et al. | |
| 2010/0006157 A1 | 1/2010 | Gerst | |
| 2010/0006162 A1 | 1/2010 | Rankin | |
| 2010/0019487 A1 | 1/2010 | deCler et al. | |
| 2010/0043988 A1 | 2/2010 | Hofmann et al. | |
| 2010/0155979 A1 | 6/2010 | Hofmann et al. | |
| 2010/0230950 A1 | 9/2010 | Williams et al. | |
| 2010/0295295 A1 | 11/2010 | Schmidt | |
| 2010/0301599 A1 | 12/2010 | Jensen et al. | |
| 2011/0012340 A1 | 1/2011 | Packham et al. | |
| 2011/0062701 A1 | 3/2011 | Downs et al. | |
| 2011/0121035 A1 | 5/2011 | Greter et al. | |
| 2011/0127767 A1 | 6/2011 | Wicks et al. | |
| 2011/0204621 A1 | 8/2011 | Whitaker et al. | |
| 2011/0204622 A1 | 8/2011 | Lewis et al. | |
| 2011/0210541 A1 | 9/2011 | Lewis et al. | |
| 2012/0031515 A1 | 2/2012 | Whitaker | |
| 2012/0068457 A1 | 3/2012 | Pisula, Jr. et al. | |
| 2012/0161051 A1 | 6/2012 | Williams et al. | |
| 2012/0179052 A1 | 7/2012 | Wilhelm et al. | |
| 2012/0259237 A1 | 10/2012 | Axelrod | |
| 2013/0030387 A1 | 1/2013 | Williams et al. | |
| 2013/0092271 A1 | 4/2013 | Downs et al. | |
| 2013/0099489 A1 | 4/2013 | Williams et al. | |
| 2013/0207380 A1 | 8/2013 | Williams et al. | |
| 2013/0289517 A1 | 10/2013 | Williams et al. | |
| 2013/0333767 A1 | 12/2013 | Schmidt | |
| 2014/0060675 A1 | 3/2014 | Wilhelm et al. | |
| 2014/0260554 A1 | 9/2014 | Rankin | |
| 2014/0261819 A1 | 9/2014 | Vranish | |
| 2015/0028586 A1 | 1/2015 | Gerst et al. | |
| 2015/0076815 A1 | 3/2015 | Lombardi, III et al. | |
| 2015/0090915 A1 | 4/2015 | Vranish | |
| 2015/0135502 A1 | 5/2015 | Rankin et al. | |
| 2015/0231369 A1 | 8/2015 | Gray et al. | |
| 2015/0260325 A1 | 9/2015 | Quick | |
| 2015/0276111 A1 | 10/2015 | Ira et al. | |
| 2016/0018037 A1 | 1/2016 | Nichols et al. | |
| 2016/0033068 A1 | 2/2016 | Wilhelm | |
| 2016/0046130 A1 | 2/2016 | Burdge et al. | |
| 2016/0047503 A1 * | 2/2016 | Ballard et al. | F16L 37/34 |
| | | | 251/149.7 |
| 2016/0102791 A1 | 4/2016 | Johnson et al. | |
| 2016/0208971 A1 | 7/2016 | Lewis et al. | |
| 2016/0208972 A1 | 7/2016 | Lewis et al. | |
| 2016/0243348 A1 | 8/2016 | Williams et al. | |
| 2016/0305574 A1 | 10/2016 | Burdge | |
| 2017/0009919 A1 | 1/2017 | Lewis et al. | |

OTHER PUBLICATIONS

U.S. Appl. No. 62/280,354, filed Jan. 19, 2016.
U.S. Appl. No. 62/299,499, filed Feb. 24, 2016.
U.S. Appl. No. 15/410,636, filed Jan. 19, 2017.
PCT International Patent Application No. PCT/US2017/014189, filed Jan. 19, 2017.

* cited by examiner

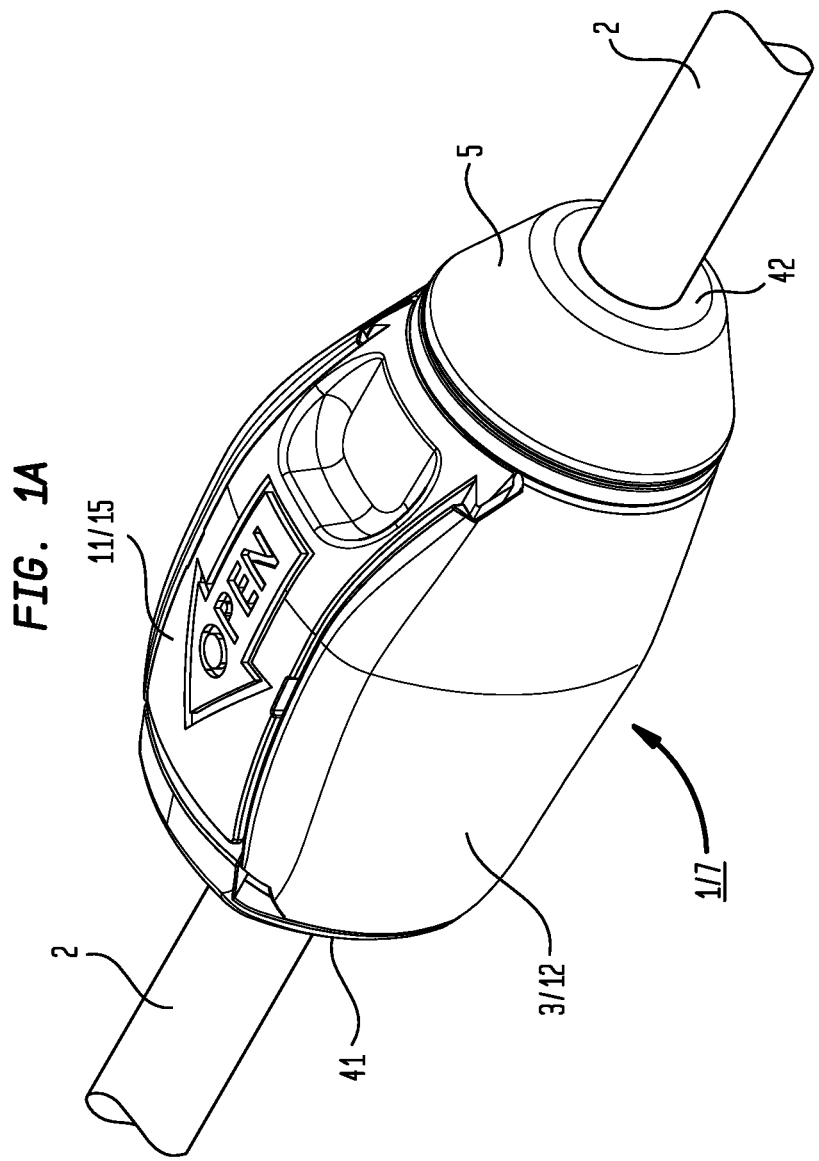

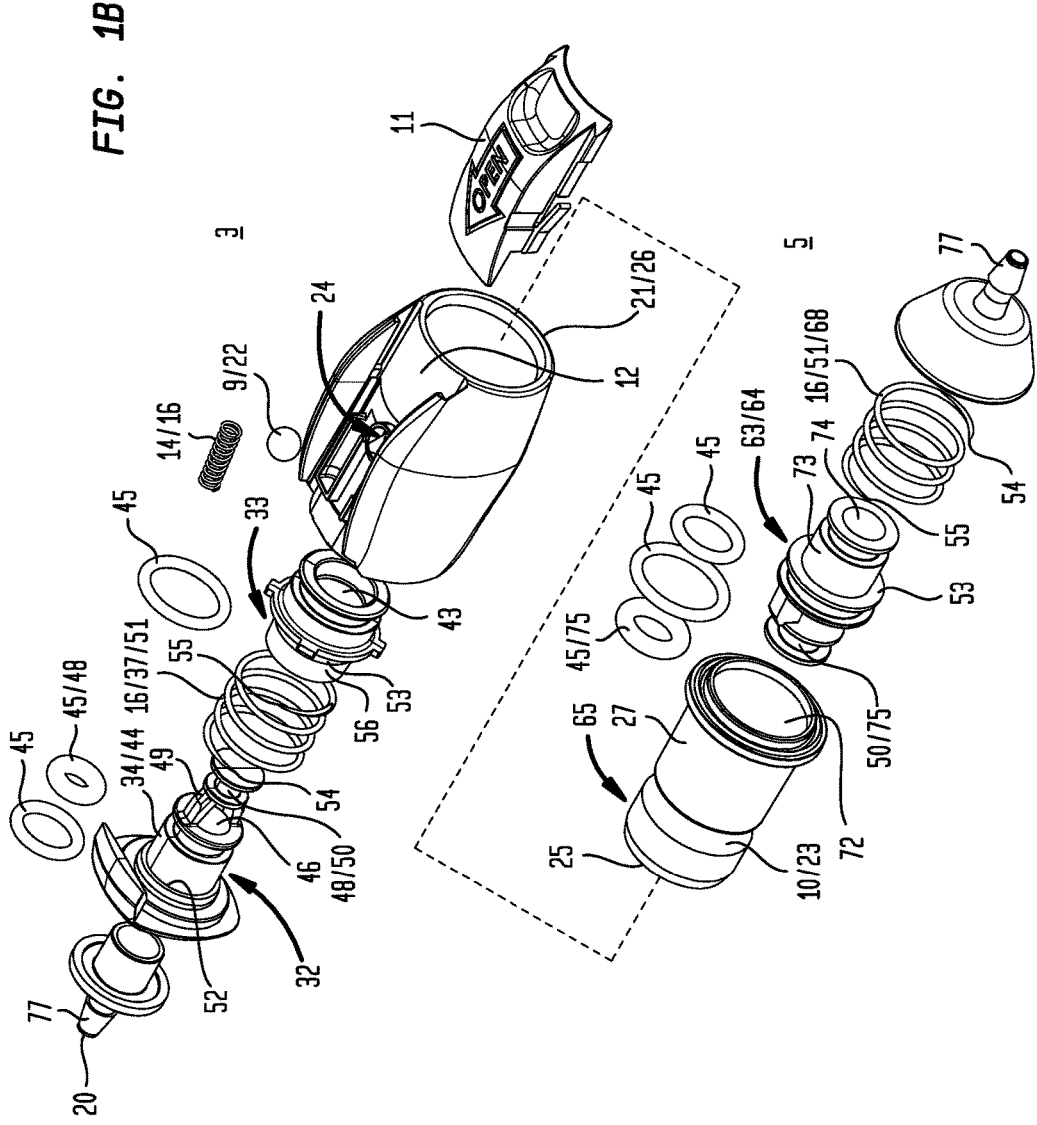

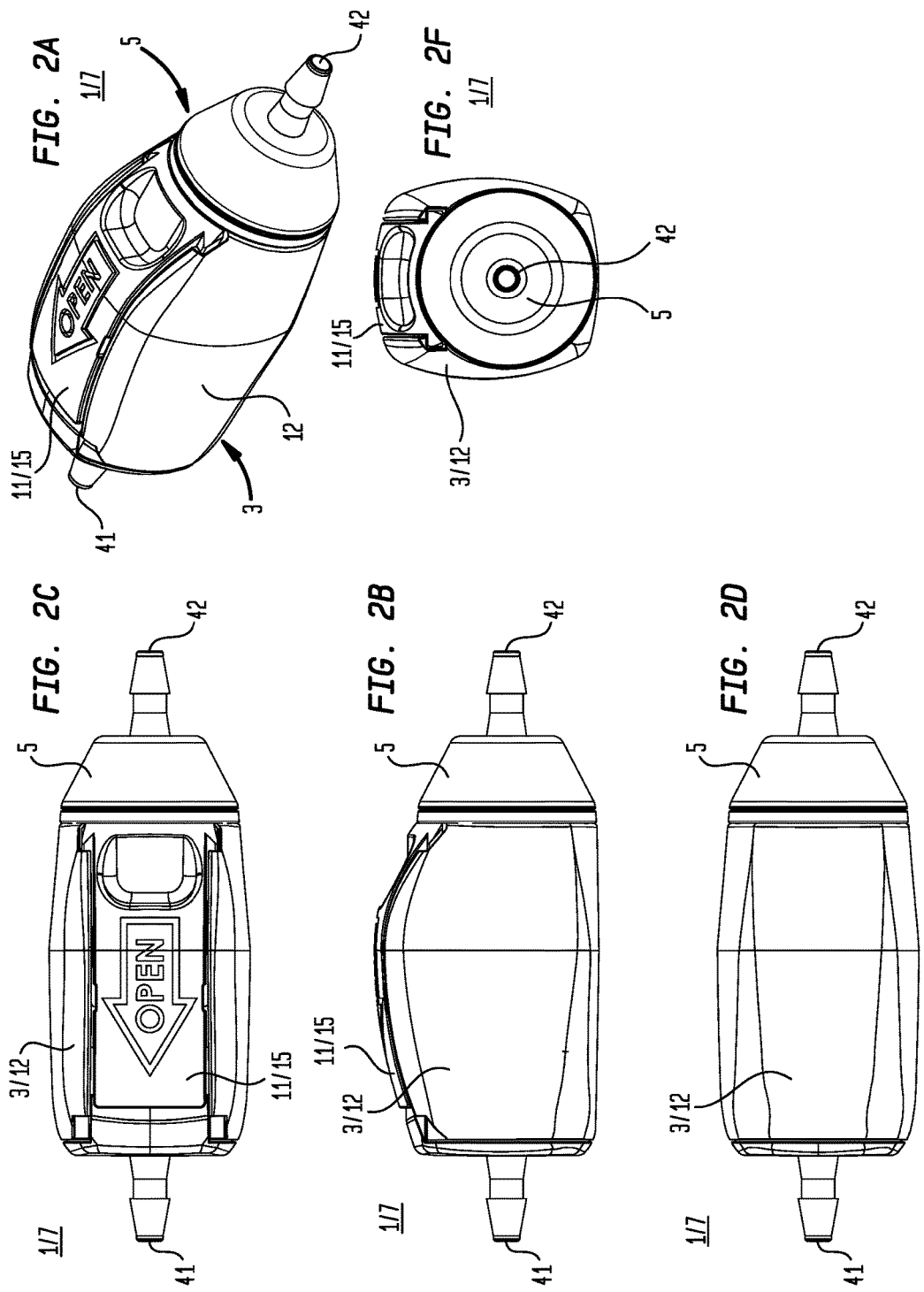

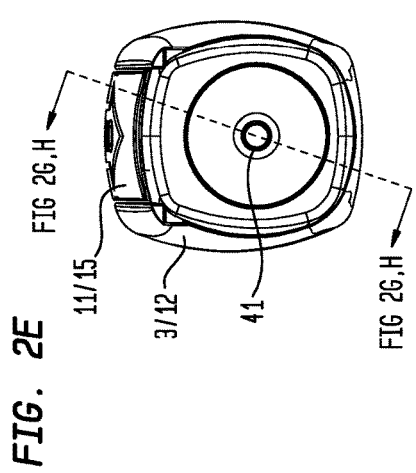
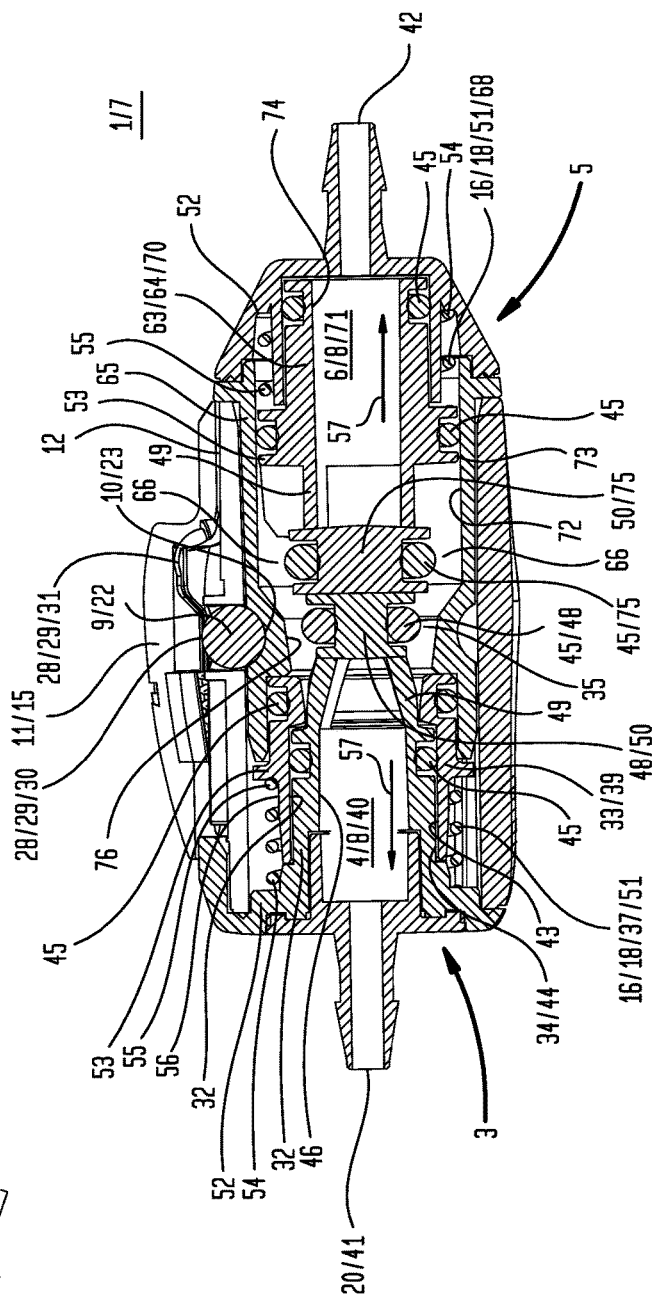

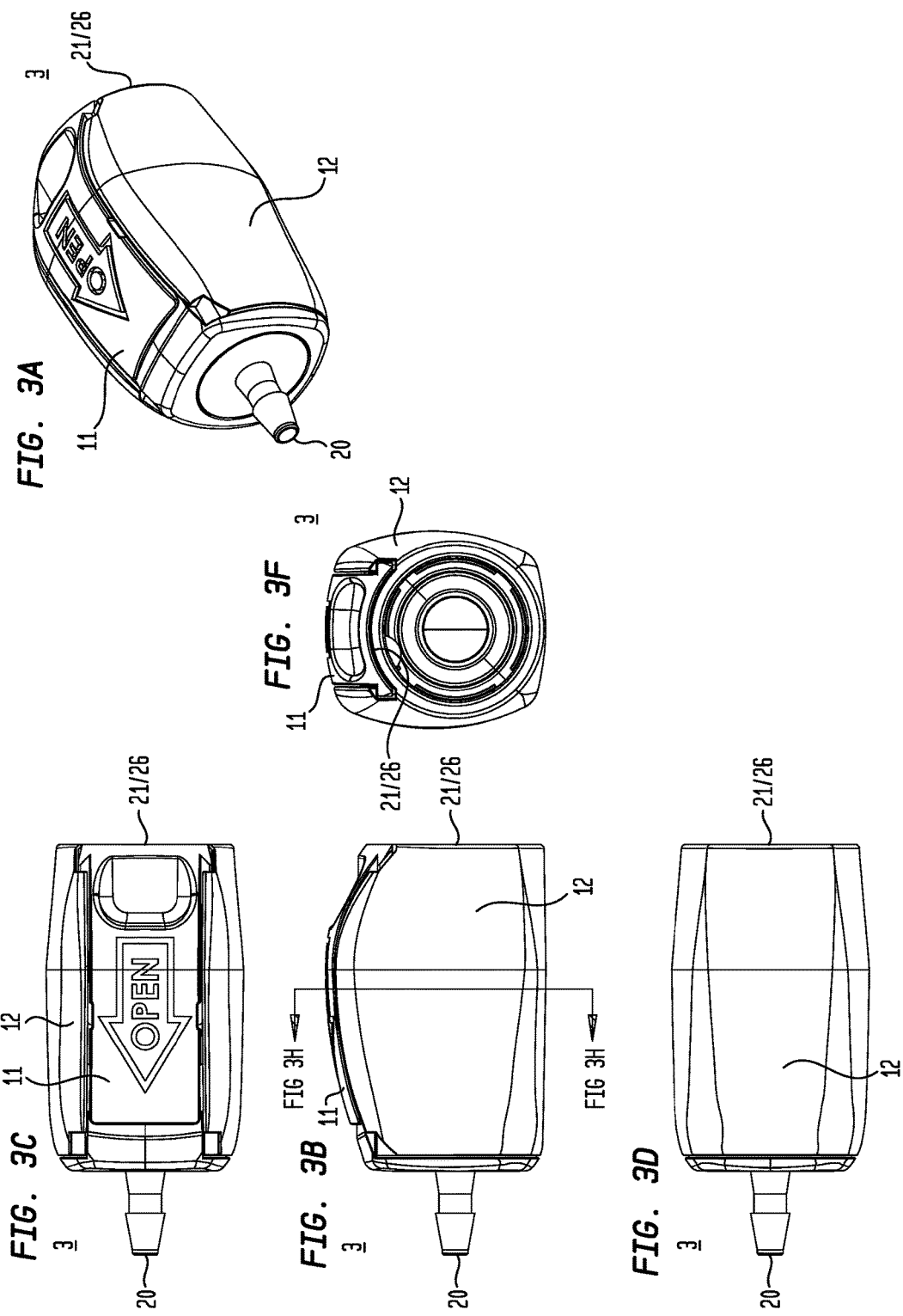

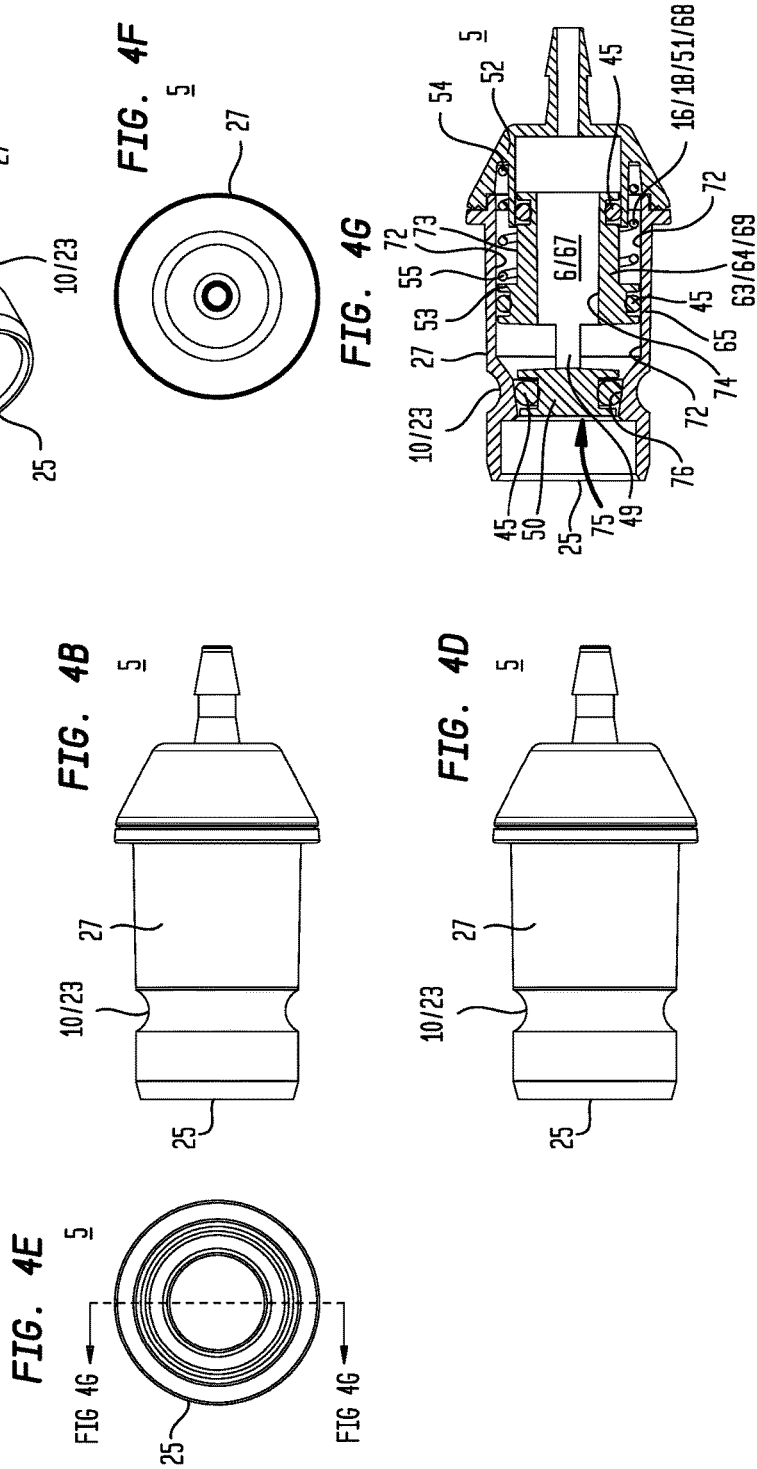

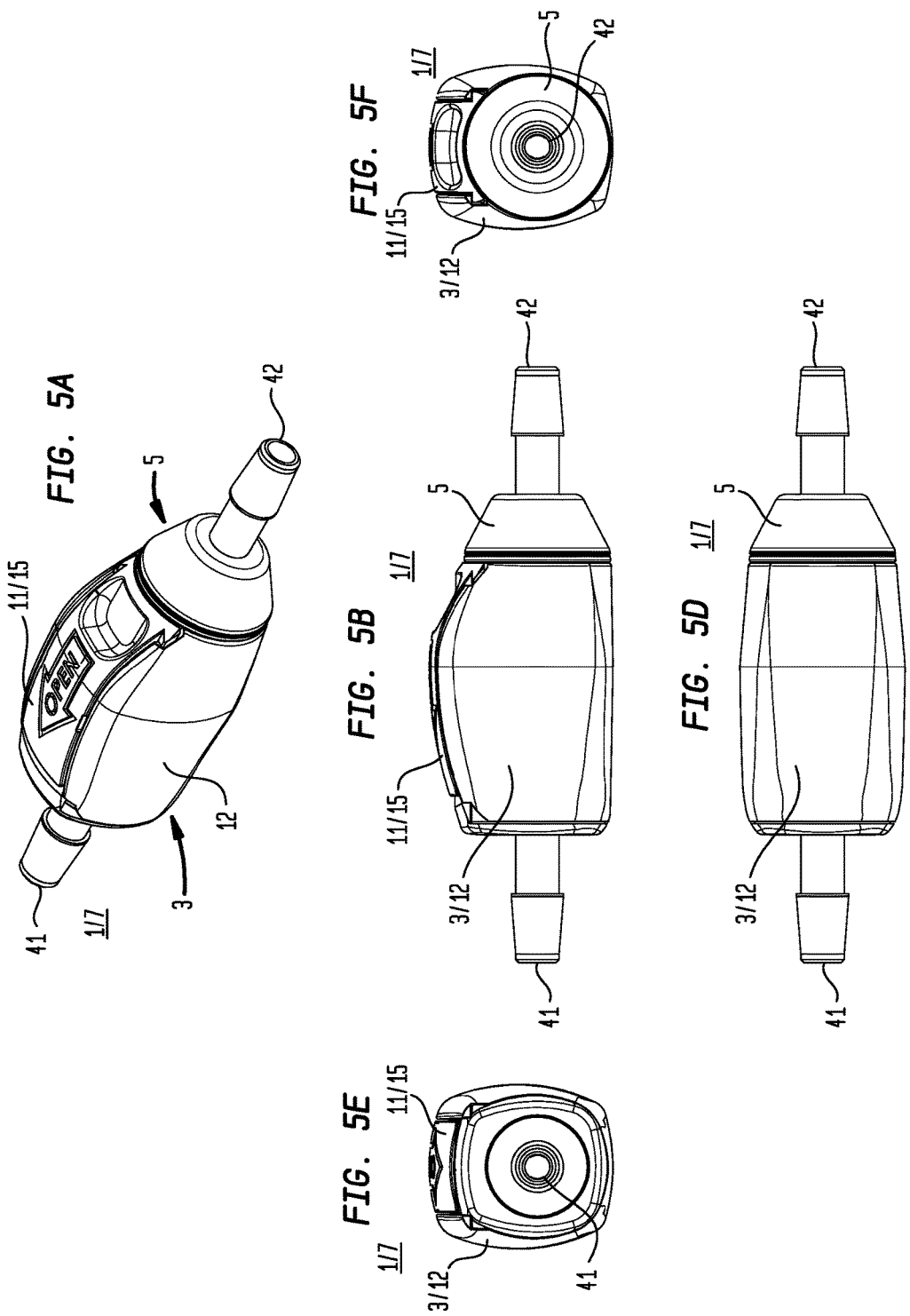

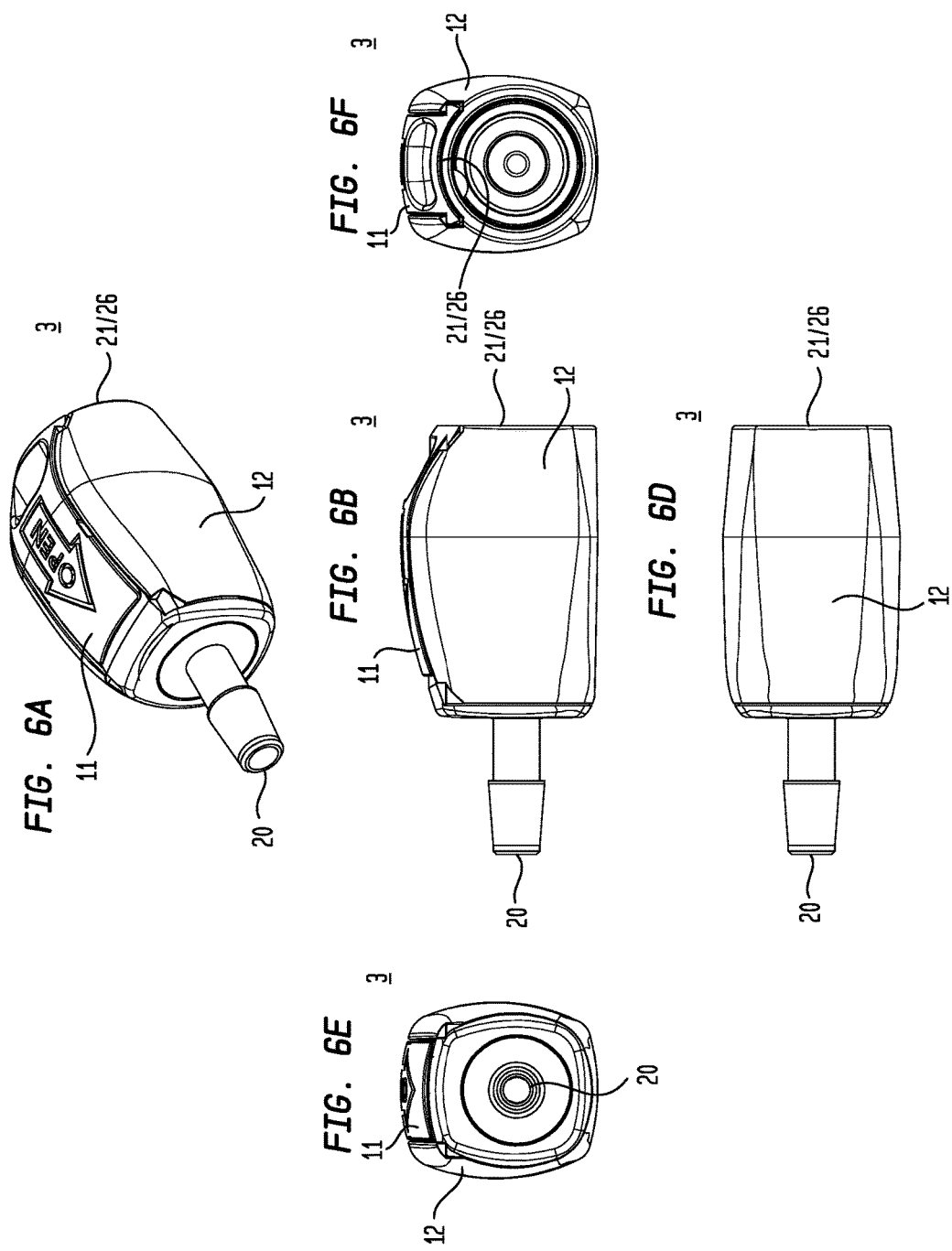

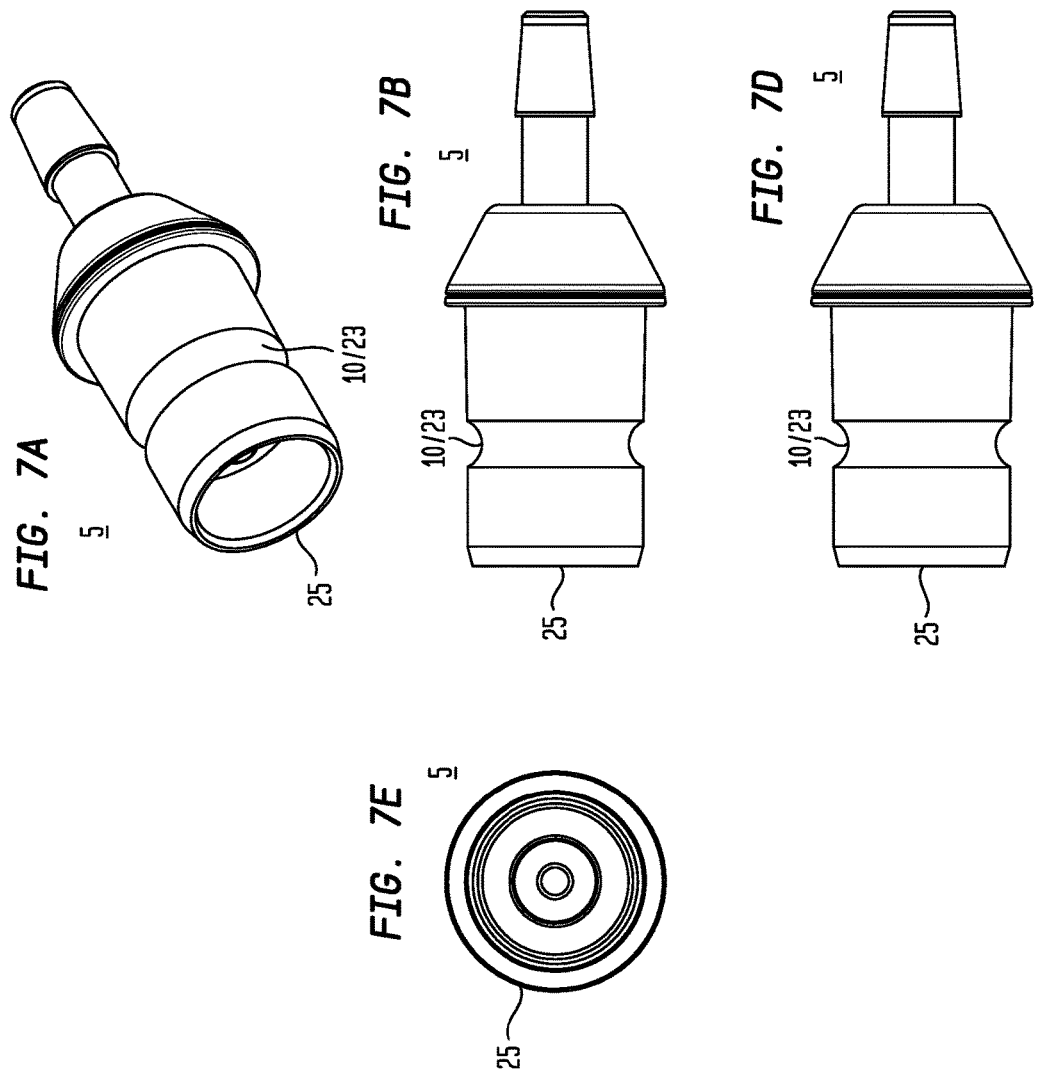

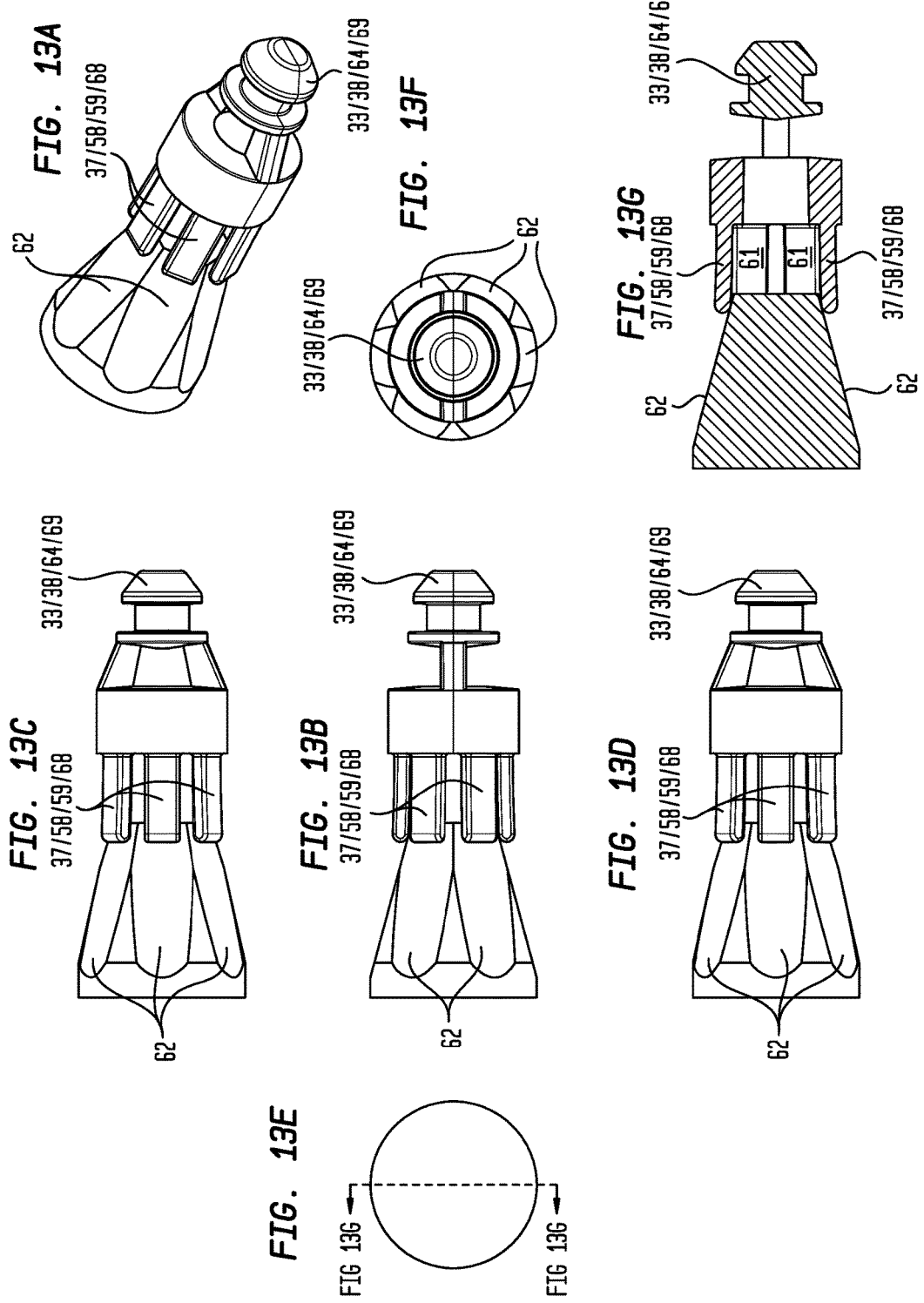

US 10,293,150 B2

CONNECTOR SYSTEM FOR RELEASABLY CONNECTING FLUID CONDUITS

This U.S. Patent Application is a continuation of U.S. patent application Ser. No. 15/410,636, filed Jan. 19, 2017, now U.S. Pat. No. 10,173,046, which claims the benefit of U.S. Provisional Patent Application No. 62/299,499, filed Feb. 24, 2016, and U.S. Provisional Patent Application No. 62/280,354, filed Jan. 19, 2016, each hereby incorporated by reference herein.

I. SUMMARY OF THE INVENTION

A broad object of a particular embodiment of the invention can be to provide a connector system for releasably connecting together tubes, for example medical tubing, and methods of making and using such a connector system, whereby the connector system includes a female coupler having a first passageway, a male coupler having a second passageway, a catch movably coupled to the female coupler, and a catch-receiving element coupled to the male coupler. Upon releasable matable axial coupling of the female and male couplers, the catch engages with the catch-receiving element to fix an axial position of the female coupler in relation to the male coupler, thereby achieving a connected condition of the connector system in which the first and second passageways dispose in fluidic communication to provide a fluid flow path. The connector system further includes a release element movably coupled to the female coupler, whereby travel of the release element along or over a female coupler outer surface of the female coupler disengages the catch from the catch-receiving element to achieve a disconnected condition of the connector system.

Another broad object of a particular embodiment of the invention can be to provide the connector system as described above, further including at least one valve operable to interrupt fluid flow through a passageway, whereby the valve is biased by a valve-biasing member disposed external to or outside of the passageway and accordingly, external to or outside of the fluid flow path when the female and male couplers releasably matably couple to achieve the connected condition of the connector system.

Naturally, further objects of the invention are disclosed throughout other areas of the specification, drawings, and claims.

II. A BRIEF DESCRIPTION OF THE DRAWINGS

FIG. 1A is an illustration of a method of using a particular embodiment of the connector system.

FIG. 1B is an exploded perspective view of the particular embodiment of the connector system shown in FIG. 1A and FIG. 2A through FIG. 4G.

FIG. 2A is a perspective view of a particular embodiment of the connector system, whereby first and male couplers are releasably matably engaged.

FIG. 2B is a side view of the particular embodiment of the connector system shown in FIG. 2A.

FIG. 2C is a top view of the particular embodiment of the connector system shown in FIG. 2A.

FIG. 2D is a bottom view of the particular embodiment of the connector system shown in FIG. 2A.

FIG. 2E is a first end view of the particular embodiment of the connector system shown in FIG. 2A.

FIG. 2F is a second end view of the particular embodiment of the connector system shown in FIG. 2A.

FIG. 2G is a cross-sectional view of the particular embodiment of the connector system shown in FIG. 2E, whereby first and male couplers are releasably matably engaged.

FIG. 3A is a perspective view of a particular embodiment of a female coupler of the connector system.

FIG. 3B is a side view of the female coupler of the connector system shown in FIG. 3A.

FIG. 3C is a top view of the female coupler of the connector system shown in FIG. 3A.

FIG. 3D is a bottom view of the female coupler of the connector system shown in FIG. 3A.

FIG. 3F is a second end view of the female coupler of the connector system shown in FIG. 3A.

FIG. 4A is a perspective view of a particular embodiment of a male coupler of the connector system.

FIG. 4B is a side view of the male coupler of the connector system shown in FIG. 4A.

FIG. 4C is a top view of the male coupler of the connector system shown in FIG. 4A.

FIG. 4D is a bottom view of the male coupler of the connector system shown in FIG. 4A.

FIG. 4E is a first end view of the male coupler of the connector system shown in FIG. 4A.

FIG. 4F is a second end view of the male coupler of the connector system shown in FIG. 4A.

FIG. 4G is a cross-sectional view of the male coupler of the connector system shown in FIG. 4E.

FIG. 5A is a perspective view of a particular embodiment of the connector system, whereby first and male couplers are releasably matably engaged.

FIG. 5B is a side view of the particular embodiment of the connector system shown in FIG. 5A.

FIG. 5D is a bottom view of the particular embodiment of the connector system shown in FIG. 5A.

FIG. 5E is a first end view of the particular embodiment of the connector system shown in FIG. 5A.

FIG. 5F is a second end view of the particular embodiment of the connector system shown in FIG. 5A.

FIG. 6A is a perspective view of a particular embodiment of a female coupler of the connector system.

FIG. 6B is a side view of the female coupler of the connector system shown in FIG. 6A.

FIG. 6D is a bottom view of the female coupler of the connector system shown in FIG. 6A.

FIG. 6E is a first end view of the female coupler of the connector system shown in FIG. 6A.

FIG. 6F is a second end view of the female coupler of the connector system shown in FIG. 6A.

FIG. 7A is a perspective view of a particular embodiment of a male coupler of the connector system.

FIG. 7B is a side view of the male coupler of the connector system shown in FIG. 7A.

FIG. 7D is a bottom view of the male coupler of the connector system shown in FIG. 7A.

FIG. 7E is a first end view of the male coupler of the connector system shown in FIG. 7A.

FIG. 7F is a second end view of the male coupler of the connector system shown in FIG. 7A.

FIG. 13A is a perspective view of a particular embodiment of a valve-biasing member configured as a resiliently flexible member disposed in axially-adjacent relation to an angled surface, whereby the resiliently flexible member is in a non-flexed condition.

FIG. 13B is a side view of the particular embodiment of the valve-biasing member shown in FIG. 13A.

FIG. 13C is a top view of the particular embodiment of the valve-biasing member shown in FIG. 13A.

FIG. 13D is a bottom view of the particular embodiment of the valve-biasing member shown in FIG. 13A.

FIG. 13E is a first end view of the particular embodiment of the valve-biasing member shown in FIG. 13A.

FIG. 13F is a second end view of the particular embodiment of the valve-biasing member shown in FIG. 13A.

FIG. 13G is a cross-sectional view of the particular embodiment of the valve-biasing member shown in FIG. 13E.

III. DETAILED DESCRIPTION OF THE PREFERRED EMBODIMENTS

Figure 2H:
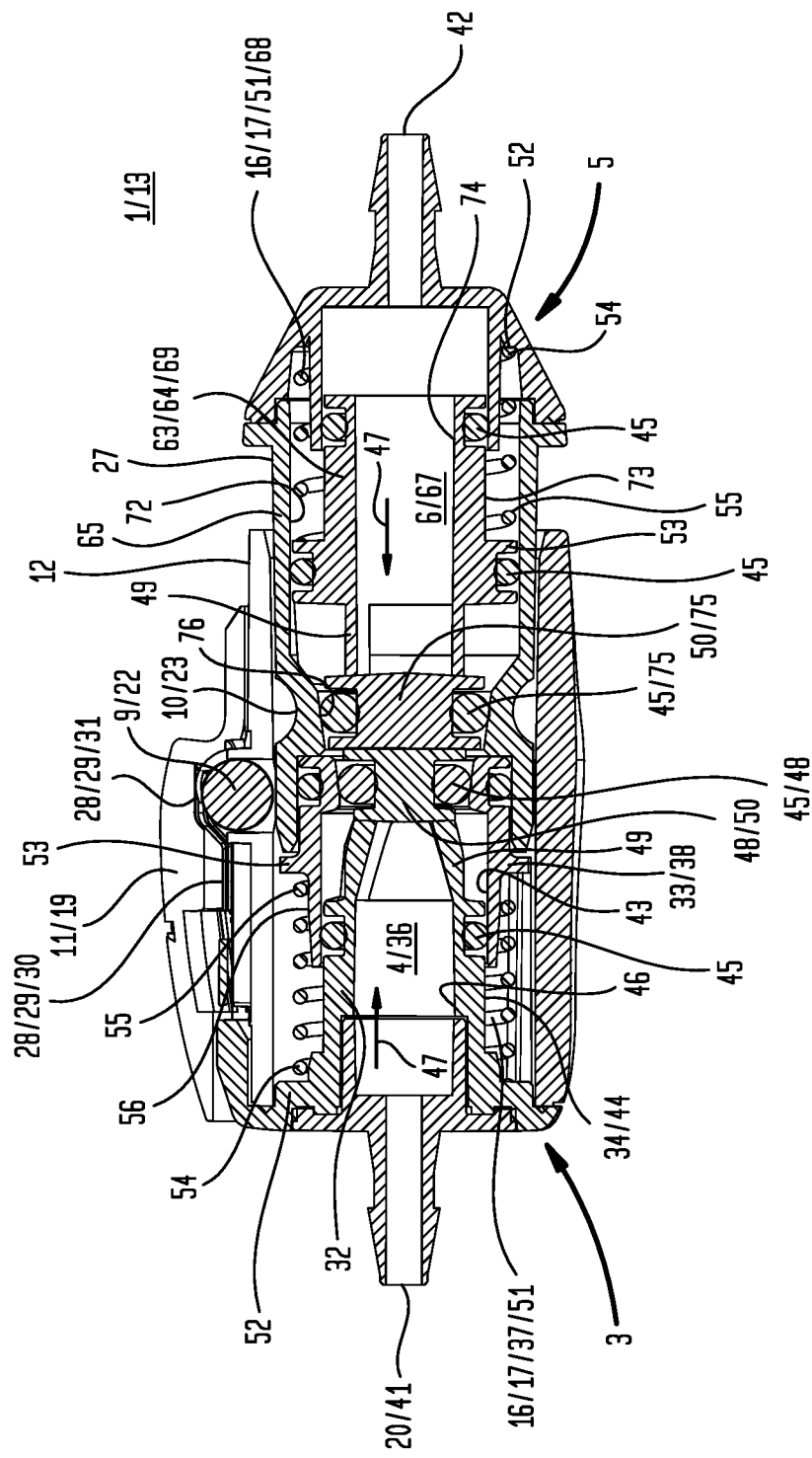
FIG. 2H is a cross-sectional view of the particular embodiment of the connector system shown in FIG. 2E, whereby first and male couplers are in adjacent axial relation but are not releasably matably engaged.

Now referring primarily to FIG. 1A, which illustrates a method of using a particular embodiment of a connector system (1) for releasably connecting together tubes (2), such as medical tubing employed in a bio-medical environment.

Advantageously, the connector system (1) can be relatively easily and securely connected, and yet relatively easily intentionally disconnected.

Now referring primarily to FIG. 1B through FIG. 7F, the connector system (1) includes a female coupler (3) having a first passageway (4) and a male coupler (5) having a second passageway (6). Upon releasable matable axial (or longitudinal) coupling of the female and male couplers (3)(5) (or, stated more concisely, upon connection of the female and male couplers (3)(5)), a connected condition (7) of the connector system (1) is achieved, disposing the first and second passageways (4)(6) in fluidic communication to provide a fluid flow path (8).

For the purposes of the present invention, a longitudinal direction can considered parallel to the first passageway (4), the second passageway (6), and/or the fluid flow path (8).

As to particular embodiments, the connector system (1) can further include a catch (9) movably coupled to the female coupler (3) and a catch-receiving element (10) coupled to the male coupler (5). Upon connection of the female and male couplers (3)(5), the catch (9) engages with the catch-receiving element (10) to fix an axial position of the female coupler (3) in relation to the male coupler (5), thereby achieving the connected condition (7) of the connector system (1).

As to particular embodiments, the connector system (1) can further include a release element (11) movably coupled to the female coupler (3), whereby travel of the release element (11) along or over a female coupler outer surface (12) of the female coupler (3) disengages the catch (9) from the catch-receiving element (10) to achieve a disconnected condition (13) of the connector system (1).

For the purposes of the present invention, the term "catch" means a restraint which, upon matable engagement with a catch-receiving element (10), can function to partially or completely restrain travel of an associated component, such as a female coupler (3).

For the purposes of the present invention, the term "catch-receiving element" means a restraint which, upon matable engagement with a catch (9), can function to partially or completely restrain travel of an associated component, such as a male coupler (5).

As to particular embodiments, the connector system (1) can be configured to provide a connection indicium upon successful releasable matable axial coupling of the female and male couplers (3)(5) to achieve the connected condition (7), whereby the connection indicium can be a visible indicium, an audible indicium, a tactile indicium, or the like, or combinations thereof.

Release Element

Now referring primarily to FIG. 2G, FIG. 2H, and FIG. 3G through FIG. 3I, as to particular embodiments, the release element (11) can be configured as a cam and the catch (9) can function as a follower, whereby the release element (11) can transform input motion into reciprocating motion of the catch (9).

For the purposes of the present invention, the term "cam" means a movable element in a mechanical linkage, whereby the cam can have an irregular periphery and may be useful in transforming motion, for example transforming motion in a first direction into motion in a second direction.

For the purposes of the present invention, the term "follower" means a movable element in a mechanical linkage, whereby movement of the follower results from movement of the cam.

For example, linear or sliding motion of the release element (11) along the female coupler outer surface (12) can be transformed into inward or outward motion of the catch (9) such that the catch (9) can move either inwardly toward the interior of the female coupler (3) or outwardly away from the interior of the female coupler (3).

The release element (11) can be biased by a release element-biasing member (14) which biases the release element (11) toward a release element first position (15), as shown in the examples of FIG. 2G and FIG. 3G through FIG. 3I.

As to particular embodiments, when in the release element first position (15), the release element (11) can bias the catch (9) inwardly toward the interior of the female coupler (3) to engage the catch (9) with the catch-receiving element (10) and achieve the connected condition (7) of the connector system (1).

As but one illustrative example, the release element-biasing member (14) can be configured as a resiliently compressible member (16), such as a spring (for example, a coil spring), whereby when the resiliently compressible member (16) disposes in a non-compressed condition (17), which is the normal biased condition, the release element (11) disposes in the release element first position (15). However, the release element-biasing member (14) need not be limited to this particular configuration.

Now referring primarily to FIG. 2H, upon forcible urging, the resiliently compressible member (16) can be compressed toward a compressed condition (18), disposing the release element (11) in a release element second position (19), allowing the catch (9) to outwardly move away from the interior of the female coupler (3) and disengage with the catch-receiving element (10) to achieve the disconnected condition (13) of the connector system (1).

Travel of the release element (11) along or over the female coupler outer surface (12) can be achieved by the application of forces directed along or over the female coupler outer surface (12), such as forces directed at an angle of between 0° to about ±45° in relation to the female coupler outer surface (12). This is in stark contrast to conventional "quick release" couplers which typically have a release element configured to travel upon the application of forces directed along an axis generally normal (or generally perpendicular) to the coupler outer surface, whereby one illustrative example of this type of release element is a pushbutton release element or a depressible release element. The instant release element (11) is advantageous over the conventional art, as only forces directed at an angle of between 0° to about ±45° in relation to the female coupler outer surface (12) can disengage the catch (9) from within the catch-receiving element (10) to achieve the disconnected condition (13) of the connector system (1), thus precluding inadvertent disconnecting by forces unintentionally applied at an angle of between about ±45° to about 90° in relation to the female coupler outer surface (12).

Now referring primarily to FIG. 2A through FIG. 3I and FIG. 8A through FIG. 8D, as to particular embodiments, travel of the release element (11), which can forcibly urge the resiliently compressible member (16) toward the compressed condition (18), can be longitudinal travel along the female coupler outer surface (12). As but one illustrative example, the longitudinal travel can be between female coupler first and second ends (20)(21).

As to particular embodiments, the longitudinal travel can be sliding travel along the female coupler outer surface (12). Further, as to particular embodiments, the longitudinal travel can be linear or generally parallel to the female coupler outer surface (12), having an angle of about 0° in relation to the female coupler outer surface (12).

Now referring primarily to FIG. 9A through FIG. 12D, as to other particular embodiments, travel of the release element (11), which can forcibly urge a resiliently compressible member (16) toward a compressed condition (18), can be circumferential travel about the female coupler outer surface (12).

As to particular embodiments, the circumferential travel can be rotating travel about the female coupler outer surface (12), whereby the circumferential travel can be any amount of travel about the circumference of the female coupler outer surface (12), whether partially or completely about the circumference of the female coupler outer surface (12). Further, as to particular embodiments, the circumferential travel can be generally parallel to the female coupler outer surface (12).

Now referring primarily to FIG. 12A through FIG. 12D, as to particular embodiments, the circumferential travel can be helical travel about the female coupler outer surface (12).

Embodiment of Catch and Catch-Receiving Element

Now referring primarily to FIG. 2G, FIG. 2H, FIG. 3G, FIG. 3H, and FIG. 4G, as to particular embodiments, the catch (9) can be configured a spherical element, such as a ball (22), and the catch-receiving element (10) can be configured as a retention groove (23) configured to receive a portion or an entirety of the ball (22). However, the catch (9) and catch-receiving element (10) need not be limited to these particular configurations and can be configured as any matable catch (9) and catch-receiving element (10) as would be known to one of ordinary skill in the art.

The ball (22) can be movably coupled to the female coupler (3) proximate the female coupler outer surface (12). For example, the ball (22) can be movably disposed within an opening (24) defined by the female coupler outer surface (12) (as shown in the example of FIG. 1B), whereby the opening (24) can be sufficiently configured to allow movement of the ball (22) through the opening (24) and inwardly toward the interior of the female coupler (3) or outwardly away from the interior of the female coupler (3). Further, the ball (22) can be movably coupled to the female coupler (3) beneath the release element (11).

The retention groove (23) can be coupled to the male coupler (5) proximate a male coupler matable end (25) which is matably received within a female coupler matable end (26) upon releasable matable axial coupling of the female and male couplers (3)(5) to provide the connected condition (7) of the connector system (1). For example, the retention groove (23) can be disposed within a male coupler outer surface (27) proximate the male coupler matable end (25).

Just as engagement of the catch (9) with the catch-receiving element (10) can fix an axial position of the female coupler (3) in relation to the male coupler (5), receipt of the ball (22) within the retention groove (23) correspondingly fixes an axial position of the female coupler (3) in relation to the male coupler (5) to achieve the connected condition (7) of the connector system (1).

Inward movement of the ball (22) can facilitate engagement of the ball (22) within the retention groove (23) upon matable reception of the male coupler matable end (25) within the female coupler matable end (26).

Conversely, outward movement of the ball (22) can facilitate disengagement of the ball (22) from within the retention groove (23), thereby allowing the female and male couplers (3)(5) to disconnect by axial movement away from one another.

Movement of the ball (22) inward and outward and correspondingly, into and out of the retention groove (23), can be controlled, at least in part, by the release element (11), whereby the release element (11) can function as a cam and the ball (22) can function as a follower (as generally described above). Accordingly, linear or sliding motion of the release element (11) along the female coupler outer surface (12) can be transformed into inward or outward movement of the ball (9), causing the ball (9) to move either inwardly toward the retention groove (23) or outwardly away from the retention groove (23).

Figure 3E:
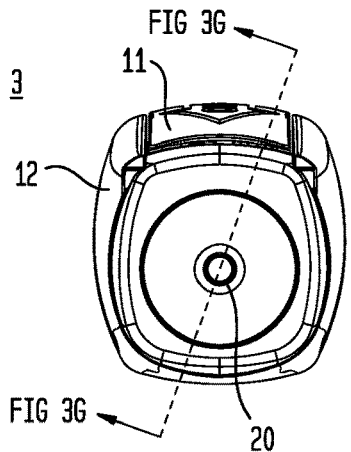
FIG. 3E is a first end view of the female coupler of the connector system shown in FIG. 3A.
Figure 3H:
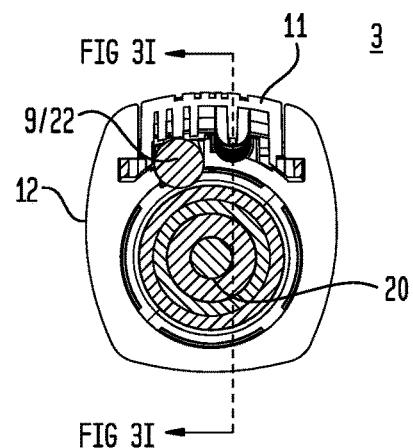
FIG. 3H is a cross-sectional view of the female coupler of the connector system shown in FIG. 3B.
Figure 3G:
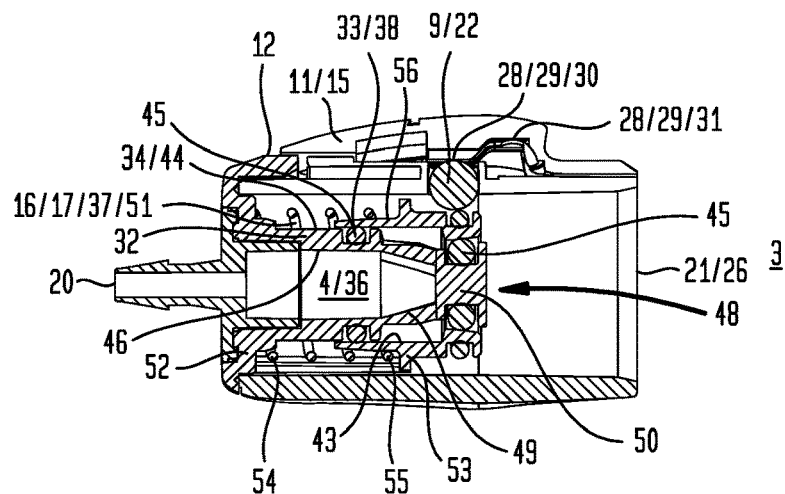
FIG. 3G is a cross-sectional view of the female coupler of the connector system shown in FIG. 3E.

Now referring primarily to FIG. 2G, FIG. 2H, and FIG. 3G, a release element inner surface (28), which disposes proximate (or adjacent) the female coupler outer surface (12), can provide a cam surface (29) having a ball locking surface (30) and a ball unlocking surface (31).

The ball locking surface (30) downwardly extends toward the female coupler outer surface (12) a greater distance than the ball unlocking surface (31), thereby disposing the ball locking surface (30) closer to the female coupler outer surface (12) than the ball unlocking surface (31). Said another way, the ball unlocking surface (31) upwardly extends away from the female coupler outer surface (12) a greater distance than the ball locking surface (30), thereby disposing the ball unlocking surface (31) farther from the female coupler outer surface (12) than the ball locking surface (30).

Correspondingly, movement of the cam surface (29) over the ball (22) to align (or contact) the ball locking surface (30) with the ball (22) biases the ball (22) inwardly and toward engagement within the retention groove (23) to achieve the connected condition (7) of the connector system (1). Conversely, movement of the cam surface (29) over the ball (22) to align (or contact) the ball unlocking surface (31) with the ball (22) permits the ball (22) to outwardly move away from the retention groove (23), thereby allowing the ball (22) to disengage from within the retention groove (23).

Now referring primarily to FIG. 2G and FIG. 3G through FIG. 3I, the release element-biasing member (14), for example a resiliently compressible member (16), can bias the release element (11) toward a release element first position (15) when in a non-compressed condition (17). When in the release element first position (15), the ball locking surface (30) aligns with (or contacts) the ball (22) and correspondingly biases the ball (22) inwardly and toward engagement within the retention groove (23) to achieve the connected condition (7) of the connector system (1).

Now referring primarily to FIG. 2H, upon forcible urging, the resiliently compressible member (16) can be compressed toward a compressed condition (18), disposing the release element (11) in a release element second position (19) in which the ball unlocking surface (31) aligns with (or contacts) the ball (22), allowing the ball (22) to outwardly move away from the retention groove (23) to achieve the disconnected condition (13) of the connector system (1).

First Valve

As to particular embodiments, the connector system (1) can further include at least one conduit and at least one valve operable to interrupt fluid flow through the conduit.

Now referring primarily to FIG. 2G, FIG. 2H, FIG. 3G, FIG. 3I, FIG. 5G, FIG. 5H, and FIG. 6G, the female coupler (3) can include a first conduit (32) defining a first passageway (4) (which as to particular embodiments, may include a fixed or removable filter) and a first valve (33) operable to interrupt fluid flow through the first passageway (4). The first valve (33) can be movable within a first valve seat (34) to sealably occlude a first port (35) in fluid communication with the first passageway (4), thereby providing a first passageway closed condition (36) in which fluid flow through the first port (35) and accordingly, through the first passageway (4), is interrupted.

The first valve (33) can be biased by a first valve-biasing member (37) which biases the first valve (33) toward a first valve closed position (38) in which the first valve (33) sealably occludes the first port (35), for example by sealably overlaying the first port (35), to provide the first passageway closed condition (36).

Now referring primarily to FIG. 2G, FIG. 2H, FIG. 3G, and FIG. 3I, as but one illustrative example, the first valve-biasing member (37) can be configured as a resiliently compressible member (16), such as a spring; however, the first valve-biasing member (37) need not be limited to this particular configuration.

Figure 3I:
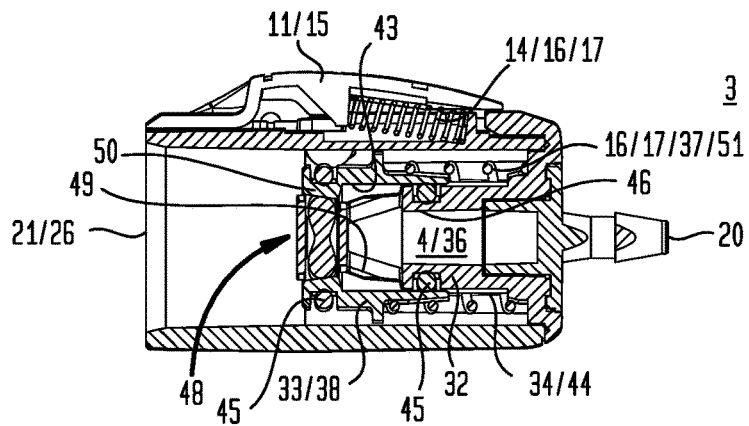
FIG. 3I is a cross-sectional view of the female coupler of the connector system shown in FIG. 3H.

When in a non-compressed condition (17), which is the normal biased condition, the resiliently compressible member (16) can bias the first valve (33) toward the first valve closed position (38) in which the first valve (33) sealably occludes the first port (35) to provide the first passageway closed condition (36) (as shown in the examples of FIG. 2H, FIG. 3G, and FIG. 3I).

Upon forcible urging, the resiliently compressible member (16) can be compressed toward a compressed condition (18), allowing the first valve (33) to travel within the first valve seat (34) away from the first port (35) toward a first valve open position (39), thus providing a first passageway open condition (40) permitting fluid flow through the first port (35) and accordingly, through the first passageway (4) (as shown in the example of FIG. 2G).

Now referring primarily to FIG. 2G, the resiliently compressible member (16) can be compressed toward the compressed condition (18) upon forcible urging resulting from connection of the female and male couplers (3)(5), thus allowing the first valve (33) to travel within the first valve seat (34) away from the first port (35) toward the first valve open position (39), thus providing the first passageway open condition (40) which permits fluid flow through the first port (35) and accordingly, through the first passageway (4). Further, upon achievement of the connected condition (7) of the connector system (1), the first passageway (4) can fluidicly communicate with the second passageway (6) of the male coupler (5) to provide the fluid flow path (8) through which fluid can flow between connector system first and second ends (41)(42).

In contrast to conventional "quick release" couplers, the instant first valve-biasing member (37) is disposed external to or outside of the first passageway (4) and accordingly, external to or outside of the fluid flow path (8) when the female and male couplers (3)(5) connect to achieve the connected condition (7) of the connector system (1). Correspondingly, fluid flowing within the fluid flow path (8) does not contact the resiliently compressible member (16), which may be advantageous for a plurality of reasons, including elimination of a potential substrate for biofilm growth within the fluid flow path (8) and elimination of a physical impediment to fluid flow within the fluid flow path (8).

Now referring primarily to FIG. 2G, FIG. 2H, FIG. 3G, and FIG. 3I, as a first illustrative example, the first valve (33) can be configured to telescopingly engage with the first conduit (32) such that the first valve (33) telescopingly disposes about the first conduit (32) and can longitudinally travel over the first conduit (32) or longitudinally slide over the first conduit (32).

With this configuration, a first valve inner surface (43) of the first valve (33) can dispose adjacent a first conduit outer surface (44) of the first conduit (32), whereby a fluid-tight seal can exist between the first valve inner surface (43) and the first conduit outer surface (44). As to particular embodiments, an o-ring (45) can be coupled to the first conduit outer surface (44), for example the o-ring (45) can be at least partially recessed within the first conduit outer surface (44), whereby when overlaid by the first valve inner surface (43), the o-ring (45) can function to provide the fluid-tight seal between the first valve inner surface (43) and the first conduit outer surface (44).

The first valve (33) can either partially or entirely surround a portion of the first conduit (32) proximate (or adjacent) the first port (35), depending upon the configuration of the first conduit (32) and the first port (35). As shown in the particular embodiment illustrated in FIG. 2G, FIG. 2H, FIG. 3G, and FIG. 3I, the first valve (33) can entirely surround a portion of the first conduit (32) proximate the first port (35) such that the first valve (33) and that portion of the first conduit (32) are coaxial. Thus, the first valve (33) and the portion of the first conduit (32) proximate the first port (35) can be disposed in concentric relation.

With this configuration, the first conduit (32) and the first valve (33) can together provide a portion of the first passageway (4). More specifically, a first conduit inner surface (46) and the first valve inner surface (43) can define a portion of the first passageway (4). As to particular embodiments, the first conduit inner surface (46) and the first valve inner surface (43) can define a first passageway (4) which is cylindrical or generally cylindrical, having a circular or generally circular cross section (as shown in the example of FIG. 3F).

Again referring primarily to FIG. 2G, FIG. 2H, FIG. 3G, and FIG. 3I, as to particular embodiments, a portion of the first conduit outer surface (44) can provide a first valve seat (34) in which the first valve (33) can move and specifically, in which the first valve (33) can longitudinally travel over the first conduit (32).

The first valve (33) can travel within the first valve seat (34) in a first direction (47) to a first valve closed position (38) in which the first valve (33) sealably occlude the first port (35) in fluid communication with the first passageway (4) (as shown in the examples of FIG. 2H, FIG. 3G, and FIG. 3I), thereby providing the first passageway closed condition (36) in which fluid flow through the first port (35) and accordingly, through the first passageway (4), is interrupted.

When in the first valve closed position (38), the first valve (33) can sealably engage with a first seal assembly (48) which is fixedly coupled to the first conduit (32) in axially spaced apart relation. For example, one or more spacers (49) can fixedly couple the first seal assembly (48) to the first conduit (32) to dispose the first seal assembly (48) in spaced apart relation to the first conduit (32) or to dispose the first seal assembly (48) a distance from the first conduit (32). To provide the first passageway closed condition (36), the first valve (33) can travel within the first valve seat (34) across the distance to sealably engage with the first seal assembly (48) and sealably occlude the first port (35) to interrupt fluid flow through the first passageway (4).

As to particular embodiments, the first conduit (32) and the first seal assembly (48) can be formed as a one-piece construct; however, the invention need not be so limited. As to particular embodiments, the first conduit (32), one or more spacers (49), and the first seal assembly (48) can be formed as a one-piece construct; however, the invention need not be so limited.

As to particular embodiments, the first seal assembly (48) can include an o-ring (45) coupled to an o-ring support (50), for example the o-ring (45) can be at least partially recessed within the o-ring support (50), whereby when overlaid by the first valve inner surface (43), the o-ring (45) can function to provide a fluid-tight seal between the first valve inner surface (43) and the first seal assembly (48).

Now referring primarily to FIG. 2G, FIG. 2H, FIG. 3G, and FIG. 3I, the first valve (33) can be biased by a first valve-biasing member (37) which biases the first valve (33) toward the first seal assembly (48) and correspondingly, toward the first valve closed position (38) to provide the first passageway closed condition (36).

As to particular embodiments, the first valve-biasing member (37) can be configured as a resiliently compressible member (16), such as a spring and for example, a coil spring or a helical spring (51). As to particular embodiments, the helical spring (51) can be disposed about a portion of the first valve (33) to entirely surround that portion of the first valve (33) such that the helical spring (51) and the first valve (33) are coaxial. Thus, the helical spring (51) and the first valve (33) can be disposed in concentric relation.

To reiterate, in contrast to conventional "quick release" couplers, the instant helical spring (51) is disposed external to or outside of the first passageway (4) and accordingly, external to or outside of the fluid flow path (8) when the female and male couplers (3)(5) connect to achieve the connected condition (7) of the connector system (1). Correspondingly, fluid flowing within the fluid flow path (8) does not contact the helical spring (51), which may be advantageous for a plurality of reasons, including elimination of a potential substrate for biofilm growth within the fluid flow path (8) and elimination of a physical impediment to fluid flow within the fluid flow path (8).

Again referring primarily to FIG. 2G, FIG. 2H, FIG. 3G, and FIG. 3I, the helical spring (51) can be disposed between a pair of projecting ribs (52)(53). For example, a helical spring first end (54) can bear against a first rib (52) outwardly extending from the first conduit outer surface (44) and an opposing helical spring second end (55) can bear against a second rib (53) outwardly extending from a first valve outer surface (56).

When in a non-compressed condition (17), which is the normal biased condition, the helical spring (51) can bias the first valve (33) toward sealable engagement with the first seal assembly (48) and correspondingly toward the first valve closed position (38) in which the first valve (33) sealably occludes the first port (35) to provide the first passageway closed condition (36).

Upon forcible urging in a second direction (57) which opposes the first direction (47), the helical spring (51) can be compressed toward a compressed condition (18), allowing the first valve (33) to travel within the first valve seat (34) away from the first seal assembly (48) and away from the first port (35) toward a first valve open position (39), thus providing a first passageway open condition (40) permitting fluid flow through the first port (35) and accordingly, through the first passageway (4) (as shown in the example of FIG. 2G).

Now referring primarily to FIG. 2G, the helical spring (51) can be compressed toward the compressed condition (18) upon forcible urging resulting from connection of the female and male couplers (3)(5), thus allowing the first valve (33) to travel within the first valve seat (34) away from the first seal assembly (48) and away from the first port (35) toward the first valve open position (39), thus providing a first passageway open condition (40) permitting fluid flow through the first port (35) and accordingly, through the first passageway (4). Further, upon achievement of the connected condition (7) of the connector system (1), the first passageway (4) can fluidicly communicate with the second passageway (6) of the male coupler (5) to provide the fluid flow path (8) through which fluid can flow between the connector system first and second ends (41)(42).

Now referring primarily to FIG. 5G, FIG. 5H, FIG. 6G, and FIG. 13A through FIG. 14G, as another illustrative example, the first valve-biasing member (37) can be configured as a resiliently flexible member (58); however, the first valve-biasing member (37) need not be limited to this particular configuration.

Figure 5C:
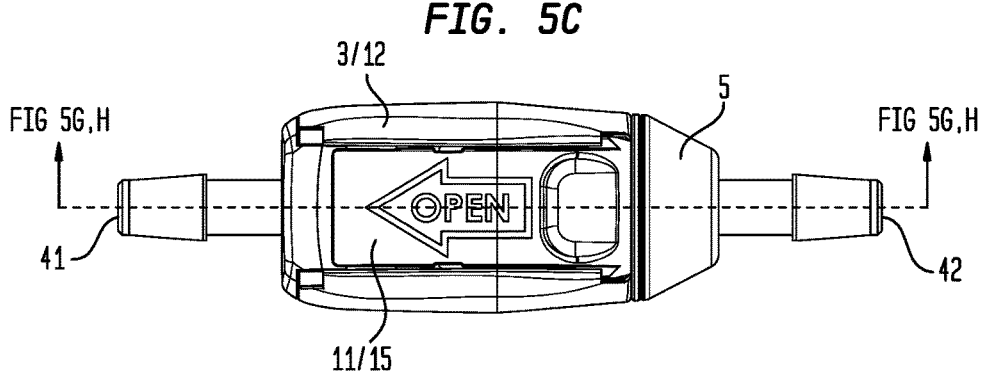
FIG. 5C is a top view of the particular embodiment of the connector system shown in FIG. 5A.
Figure 5G:
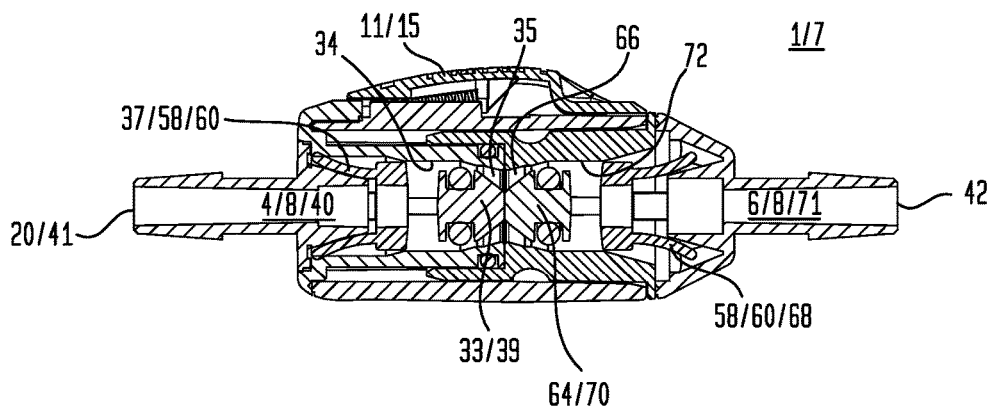
FIG. 5G is a cross-sectional view of the particular embodiment of the connector system shown in FIG. 5C, whereby first and male couplers are releasably matably engaged.
Figure 5H:
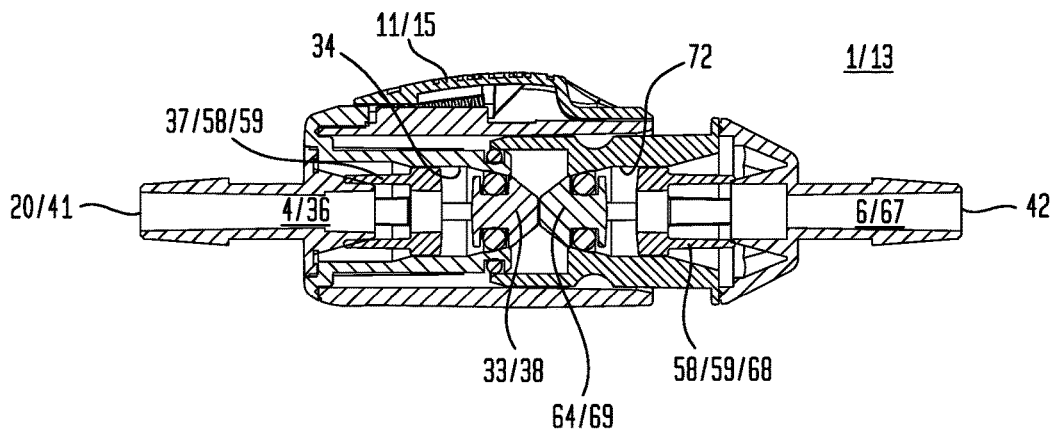
FIG. 5H is a cross-sectional view of the particular embodiment of the connector system shown in FIG. 5C, whereby first and male couplers are in adjacent axial relation but are not releasably matably engaged.
Figure 6C:
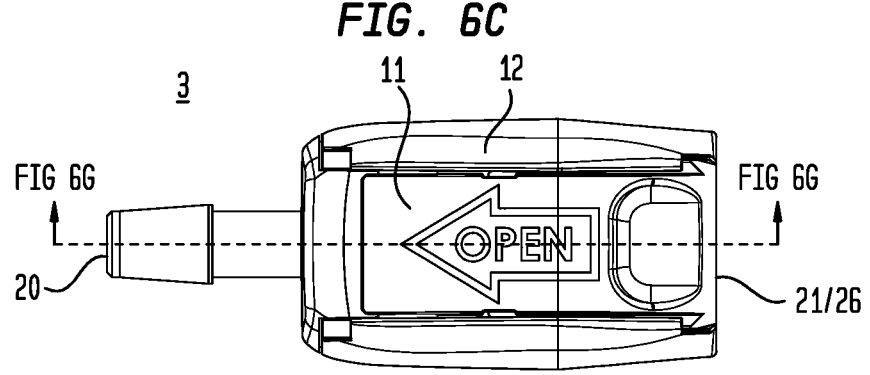
FIG. 6C is a top view of the female coupler of the connector system shown in FIG. 6A.
Figure 6G:
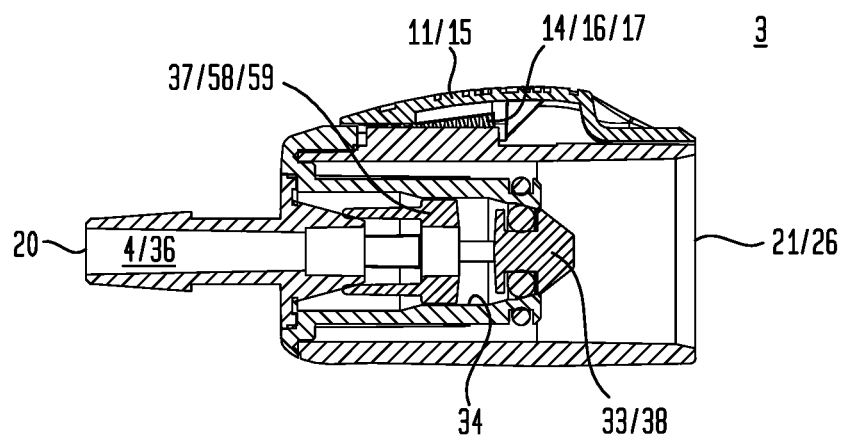
FIG. 6G is a cross-sectional view of the female coupler of the connector system shown in FIG. 6C.

When in a non-flexed condition (59) (as shown in the examples of FIG. 13A through FIG. 13G), the resiliently flexible member (58) can bias the first valve (33) toward the first valve closed position (38) in which the first valve (33) sealably occludes the first port (35) (as shown in the examples of FIG. 5H and FIG. 6G).

Upon forcible urging, the resiliently flexible member (58) can be flexed toward a flexed condition (60) (as shown in the examples of FIG. 14A through FIG. 14G), allowing the first valve (33) to travel within the first valve seat (34) toward a first valve open position (39) away from the first port (35), thereby permitting fluid flow through the first port (35) and accordingly, through the first passageway (4) to provide a first passageway open condition (40) (as shown in the example of FIG. 5G).

Now referring primarily to FIG. 5O, the resiliently flexible member (58) can be flexed toward the flexed condition (60) upon forcible urging resulting from connection of the female and male couplers (3)(5), thus allowing the first valve (33) to travel within the first valve seat (34) toward the first valve open position (39) away from the first port (35), thereby permitting fluid flow through the first port (35) and accordingly, through the first passageway (4) to provide the first passageway open condition (40). Further, upon achievement of the connected condition (7) of the connector system (1), the first passageway (4) can fluidicly communicate with the second passageway (6) of the male coupler (5) to provide the fluid flow path (8) through which fluid can flow between the connector system first and second ends (41)(42).

Now referring primarily to FIG. 13A through FIG. 14G, as to particular embodiments, the resiliently flexible member (58) can be configured as a plurality of resiliently flexible members (58) which dispose in circumferentially spaced-apart relation to define an internal space (61). Additionally, an angled surface (62) can be disposed in axially-adjacent relation to the plurality of resiliently flexible members (58).

Upon forcible urging resulting from connection of the female and male couplers (3)(5), the plurality of resiliently flexible members (58) move axially toward the angled surface (62), whereby the angled surface (62) can be received within the internal space (61) while forcibly urging the plurality of resiliently flexible members (58) to flex about the angled surface (62) toward the flexed condition (60) (as shown in the examples of FIG. 14A through FIG. 14G). Correspondingly, the first valve (33) travels within the first valve seat (34) toward the first valve open position (39) away from the first port (35), thereby permitting fluid flow through the first port (35) and accordingly, through the first passageway (4) to provide the first passageway open condition (40).

Upon uncoupling of the female and male couplers (3)(5), the plurality of resiliently flexible members (58) are biased toward the non-flexed condition (59) (as shown in the examples of FIG. 13A through FIG. 13G), biasing the first valve (33) toward the first valve closed position (38) in which the first valve (33) sealably occludes the first port (35).

Again referring primarily to FIG. 13A through FIG. 14G, as to particular embodiments, the resiliently flexible member (58) and the first valve (33) can be formed as a one-piece construct; however, the invention need not be so limited.

Second Valve

Now referring primarily to FIG. 2G, FIG. 2H, FIG. 4G, FIG. 5G, FIG. 5H, and FIG. 7G, the male coupler (5) can include a second conduit (63) defining a second passageway (6) (which as to particular embodiments, may include a fixed or removable filter) and a second valve (64) operable to interrupt fluid flow through the second passageway (6).

The second valve (64) can be movable within a second valve seat (65) to sealably occlude a second port (66) in fluid communication with the second passageway (6), thereby providing a second passageway closed condition (67) in which fluid flow through the second port (66) and accordingly, through the second passageway (6), is interrupted.

The second valve (64) can be biased by a second valve-biasing member (68) which biases the second valve (64) toward a second valve closed position (69) in which the second valve (64) sealably occludes the second port (66), for example by sealably overlaying the second port (66), to provide the second passageway closed condition (67).

Now referring primarily to FIG. 2G, FIG. 2H, and FIG. 4G, as but one illustrative example, the second valve-biasing member (68) can be configured as a resiliently compressible member (16), such as a spring; however, the second valve-biasing member (68) need not be limited to this particular configuration.

When in a non-compressed condition (17), which is the normal biased condition, the resiliently compressible member (16) can bias the second valve (64) toward the second valve closed position (69) in which the second valve (64) sealably occludes the second port (66) to provide the second passageway closed condition (67) (as shown in the examples of FIG. 2H and FIG. 4G).

Upon forcible urging, the resiliently compressible member (16) can be compressed toward a compressed condition (18), allowing the second valve (64) to travel within the second valve seat (65) away from the second port (66) toward a second valve open position (70), thus providing a second passageway open condition (71) permitting fluid flow through the second port (66) and accordingly, through the second passageway (6) (as shown in the example of FIG. 2G).

Now referring primarily to FIG. 2G, the resiliently compressible member (16) can be compressed toward the compressed condition (18) upon forcible urging resulting from connection of the female and male couplers (3)(5), thus allowing the second valve (64) to travel within the second valve seat (65) away from the second port (66) toward the second valve open position (70), thus providing a second passageway open condition (71) which permits fluid flow through the second port (66) and accordingly, through the second passageway (6). Further, upon achievement of the connected condition (7) of the connector system (1), the first passageway (4) of the female coupler (3) can fluidicly communicate with the second passageway (6) to provide the fluid flow path (8) through which fluid can flow between the connector system first and second ends (41)(42).

In contrast to conventional "quick release" couplers, the instant second valve-biasing member (68) is disposed external to or outside of the second passageway (6) and accordingly, external to or outside of the fluid flow path (8) when the female and male couplers (3)(5) connect to achieve the connected condition (7) of the connector system (1). Correspondingly, fluid flowing within the fluid flow path (8) does not contact the resiliently compressible member (16), which may be advantageous for a plurality of reasons, including elimination of a potential substrate for biofilm growth within the fluid flow path (8) and elimination of a physical impediment to fluid flow within the fluid flow path (8).

Now referring primarily to FIG. 2G, FIG. 2H, and FIG. 4G, as a first illustrative example, the second valve (64) can be provided by the second conduit (63) which can longitudinally travel or longitudinally slide within the second valve seat (65).

The second valve seat (65) can be configured to telescopingly engage with the second conduit (63) such that the second valve seat (65) telescopingly disposes about the second conduit (63) to allow longitudinal travel of the second conduit (63) within the second valve seat (65).

With this configuration, a second valve seat inner surface (72) of the second valve seat (65) can dispose adjacent a second conduit outer surface (73) of the second conduit (63), whereby a fluid-tight seal can exist between the second valve seat inner surface (72) and the second conduit outer surface (73). As to particular embodiments, an o-ring (45) can be coupled to the second conduit outer surface (73), for example the o-ring (45) can be at least partially recessed within the second conduit outer surface (73), whereby when overlaid by the second valve seat inner surface (72), the o-ring (45) can function to provide a fluid-tight seal between the second valve seat inner surface (72) and the second conduit outer surface (73).

The second valve seat (65) can either partially or entirely surround a portion of the second conduit (63) proximate (or adjacent) the second port (66), depending upon the configuration of the second conduit (63) and the second port (66). As shown in the particular embodiment illustrated in FIG. 2G, FIG. 2H, and FIG. 4G, the second valve seat (65) can entirely surround a portion of the second conduit (63) proximate the second port (66) such that the second valve seat (65) and that portion of the second conduit (63) are coaxial. Thus, the second valve seat (65) and the portion of the second conduit (63) proximate the second port (66) can be disposed in concentric relation.

With this configuration, the second conduit (63) and the second valve seat (65) can together provide a portion of the second passageway (6). More specifically, a second conduit inner surface (74) and the second valve seat inner surface (72) can define a portion of the second passageway (6). As to particular embodiments, the second conduit inner surface (74) and the second valve seat inner surface (72) can define a second passageway (6) which is cylindrical or generally cylindrical, having a circular or generally circular cross section (as shown in the example of FIG. 4E).

The second valve (64) can travel within the second valve seat (65) in a first direction (47) to a second valve closed position (69) in which the second conduit (63) sealably occludes the second port (66) in fluid communication with the second passageway (6), thereby providing a second passageway closed condition (67) in which fluid flow through the second port (66) and accordingly, through the second passageway (6), is interrupted.

When in the second valve closed position (69), a second seal assembly (75) which is fixedly coupled to the second conduit (63) in axially spaced apart relation via one or more spacers (49) can sealably engage with an engagement surface (76) provided by an inwardly tapering portion of the second valve seat inner surface (72), thus providing the second passageway closed condition (67) in which the second port (66) is sealably occluded to interrupt fluid flow through the second passageway (6).

As to particular embodiments, the second conduit (63) and the second seal assembly (75) can be formed as a one-piece construct; however, the invention need not be so limited. As to particular embodiments, the second conduit (63), one or more spacers (49), and the second seal assembly (75) can be formed as a one-piece construct; however, the invention need not be so limited.

As to particular embodiments, the second seal assembly (75) can include an o-ring (45) coupled to an o-ring support (50), for example the o-ring (45) can be at least partially recessed within the o-ring support (50), whereby when overlaid by the engagement surface (76), the o-ring can function to provide the fluid-tight seal between the engagement surface (76) and the second seal assembly (75).

Again referring primarily to FIG. 2G, FIG. 2H, and FIG. 4G, the second conduit (63) can be biased by a second valve-biasing member (68) which biases the second conduit (63) and correspondingly the second seal assembly (75) toward the engagement surface (76) and correspondingly, toward the second valve closed position (69) to provide the second passageway closed condition (67).

As to particular embodiments, the second valve-biasing member (68) can be configured as a resiliently compressible member (16), such as a spring and for example, a coil spring or a helical spring (51). As to particular embodiments, the helical spring (51) can be disposed about a portion of the second conduit (63) to entirely surround that portion of the second conduit (63) such that the helical spring (51) and the second conduit (63) are coaxial. Thus, the helical spring (51) and the second conduit (63) can be disposed in concentric relation.

To reiterate, in contrast to conventional "quick release" couplers, the instant helical spring (51) is disposed external to or outside of the second passageway (6) and accordingly, external to or outside of the fluid flow path (8) when the female and male couplers (3)(5) connect to achieve the connected condition (7) of the connector system (1). Correspondingly, fluid flowing within the fluid flow path (8) does not contact the helical spring (51), which may be advantageous for a plurality of reasons, including elimination of a potential substrate for biofilm growth within the fluid flow path (8) and elimination of a physical impediment to fluid flow within the fluid flow path (8).

Again referring primarily to FIG. 2G, FIG. 2H, and FIG. 4G, the helical spring (51) can be disposed between a pair of projecting ribs (52)(53). For example, a helical spring first end (54) can bear against a first rib (52) and an opposing helical spring second end (55) can bear against a second rib (53) outwardly extending from the second conduit outer surface (73).

When in a non-compressed condition (17), which is the normal biased condition, the helical spring (51) can bias the second conduit (63) and correspondingly the second seal assembly (75) toward the engagement surface (76) and correspondingly, toward the second valve closed position (69), thereby sealably occluding the second port (66) and providing the second passageway closed condition (67).

Upon forcible urging in a second direction (57) which opposes the first direction (47), the helical spring (51) can be compressed toward a compressed condition (18), allowing the second conduit (63) to travel within the second valve seat (65) to dispose the second seal assembly (75) away from the engagement surface (76) and away from the second port (66) toward a second valve open position (70), thus providing a second passageway open condition (71) permitting fluid flow through the second port (66) and accordingly, through the second passageway (6) (as shown in the example of FIG. 2G).

Now referring primarily to FIG. 2G, the helical spring (51) can be compressed toward the compressed condition (18) upon forcible urging resulting from connection of the female and male couplers (3)(5), thus allowing the second conduit (63) to travel within the second valve seat (65) to dispose the second seal assembly (75) away from the engagement surface (76) and away from the second port (66) toward a second valve open position (70), thus providing a second passageway open condition (71) permitting fluid flow through the second port (66) and accordingly, through the second passageway (6). Further, upon achievement of the connected condition (7) of the connector system (1), the first passageway (4) of the female coupler (3) can fluidicly communicate with the second passageway (6) to provide the fluid flow path (8) through which fluid can flow between the connector system first and second ends (41)(42).

Now referring primarily to FIG. 5G, FIG. 5H, FIG. 7G, and FIG. 13A through FIG. 14G, as another illustrative example, the second valve-biasing member (68) can be configured as a resiliently flexible member (58); however, the second valve-biasing member (68) need not be limited to this particular configuration.

Figure 7C:
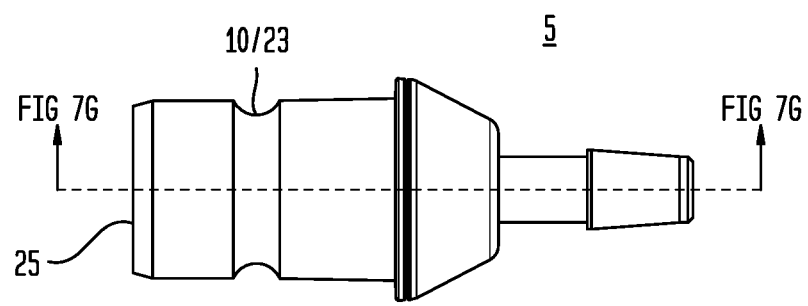
FIG. 7C is a top view of the male coupler of the connector system shown in FIG. 7A.
Figure 7G:
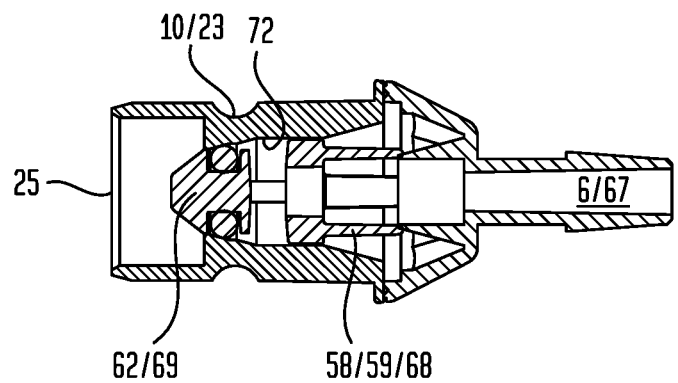
FIG. 7G is a cross-sectional view of the male coupler of the connector system shown in FIG. 7C.
Figure 8A:
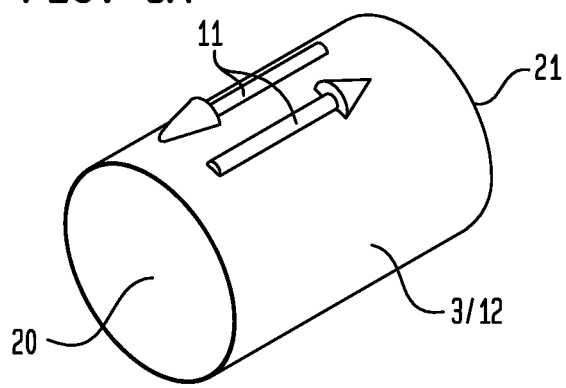
FIG. 8A is a perspective view of a release element of the connector system, whereby the release element is depicted as a pair of arrows to illustrate travel of the release element along or over a female coupler outer surface which can be achieved by the application of forces directed along or over the female coupler outer surface.
Figure 8B:
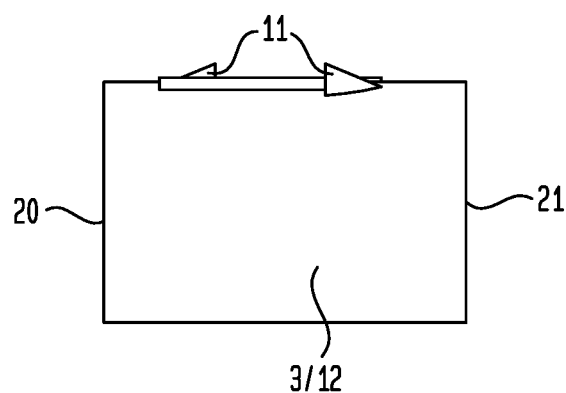
FIG. 8B is a side view of the release element of the connector system shown in FIG. 8A.
Figure 8C:
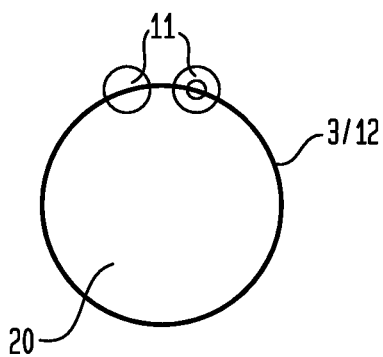
FIG. 8C is a first end view of the release element of the connector system shown in FIG. 8A.
Figure 8D:
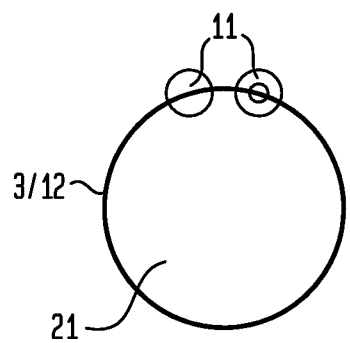
FIG. 8D is a second end view of the release element of the connector system shown in FIG. 8A.
Figure 9A:
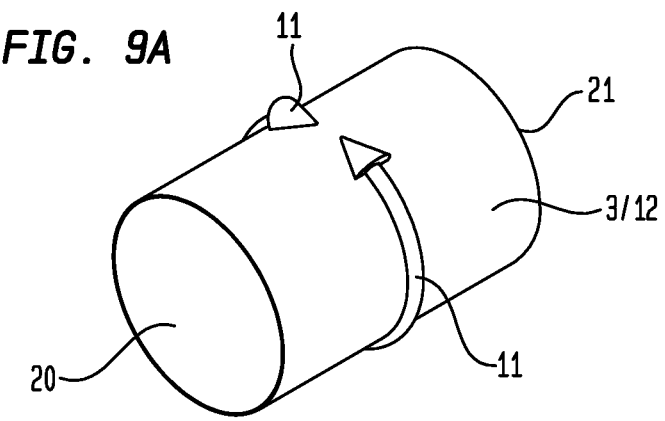
FIG. 9A is a perspective view of a release element of the connector system, whereby the release element is depicted as an arrow to illustrate circumferential travel of the release element about a female coupler outer surface which can be achieved by the application of forces directed circumferentially along or over the female coupler outer surface.
Figure 9B:
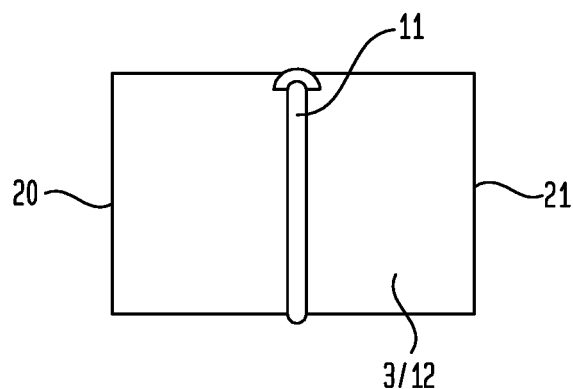
FIG. 9B is a side view of the release element of the connector system shown in FIG. 9A.
Figure 9C:
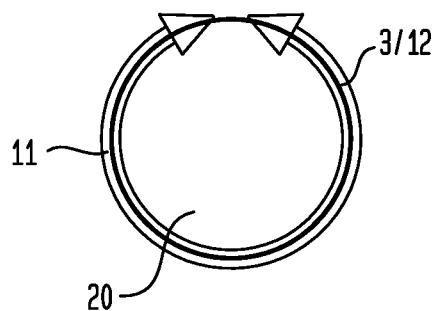
FIG. 9C is a first end view of the release element of the connector system shown in FIG. 9A.
Figure 9D:
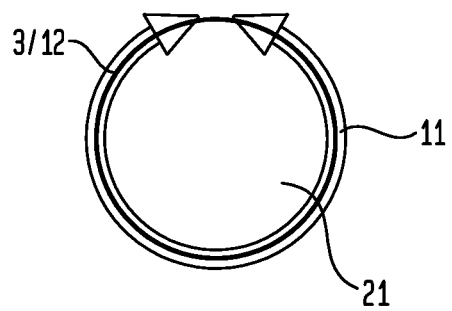
FIG. 9D is a second end view of the release element of the connector system shown in FIG. 9A.
Figure 10A:
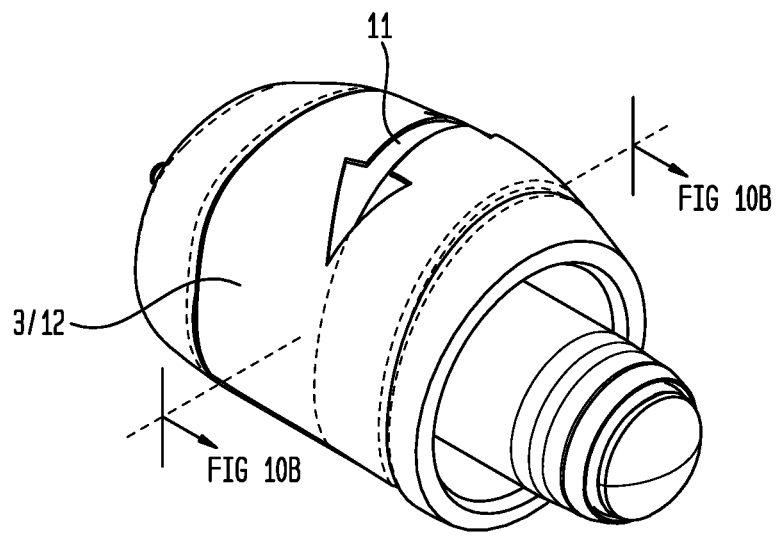
FIG. 10A is a perspective view of a release element of the connector system, whereby the release element is depicted as an arrow to illustrate circumferential travel of the release element about a female coupler outer surface which can be achieved by the application of forces directed circumferentially along or over the female coupler outer surface.
Figure 10B:
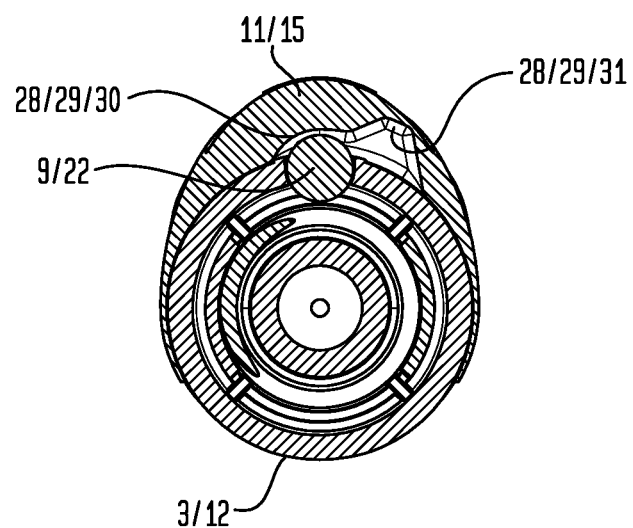
FIG. 10B is a cross sectional view of the release element of the connector system shown in FIG. 10A, whereby a catch disposes in an opening first portion defined by a release element inner surface first portion to provide a release element first position.
Figure 11A:
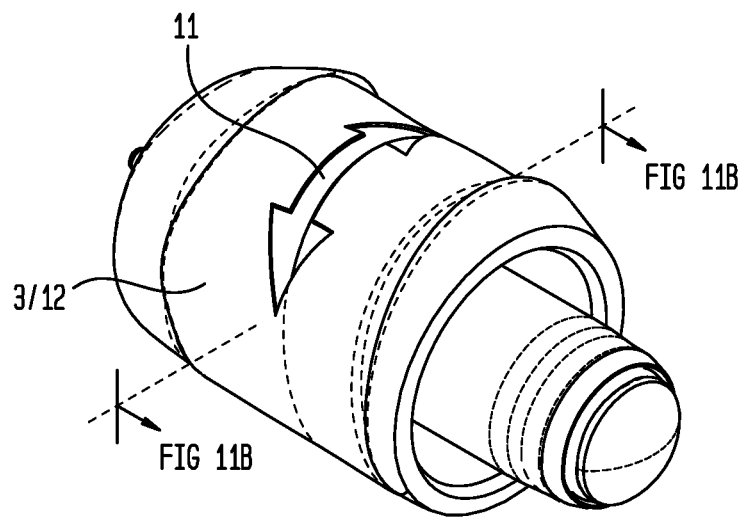
FIG. 11A is a perspective view of a release element of the connector system, whereby the release element is depicted as an arrow to illustrate circumferential travel of the release element about a female coupler outer surface which can be achieved by the application of forces directed circumferentially along or over the female coupler outer surface.
Figure 11B:
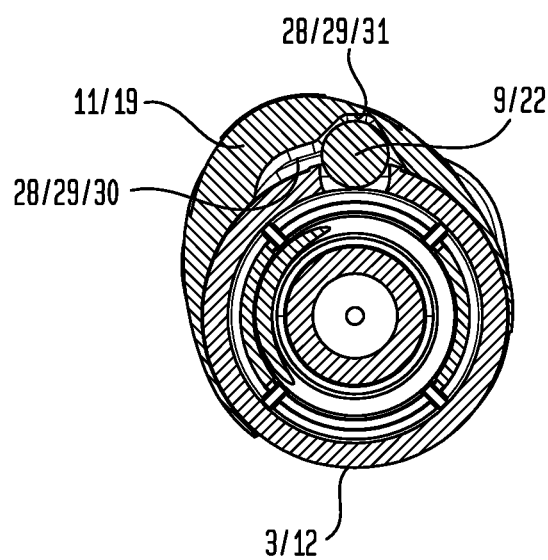
FIG. 11B is a cross sectional view of the release element of the connector system shown in FIG. 11A, whereby a catch disposes in an opening second portion defined by a release element inner surface second portion to provide a release element second position.
Figure 12A:
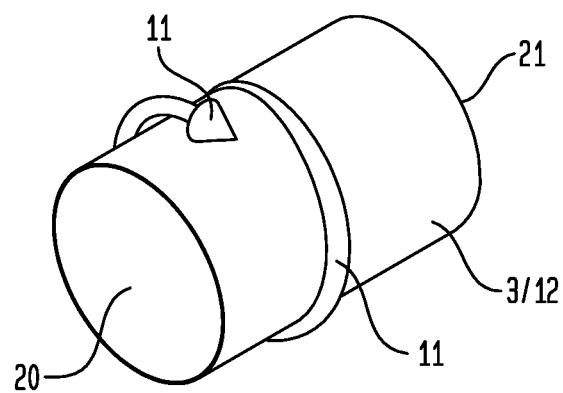
FIG. 12A is a perspective view of a release element of the connector system, whereby the release element is depicted as an arrow to illustrate helical travel of the release element about a female coupler outer surface which can be achieved by the application of forces directed helically along or over the female coupler outer surface.
Figure 12B:
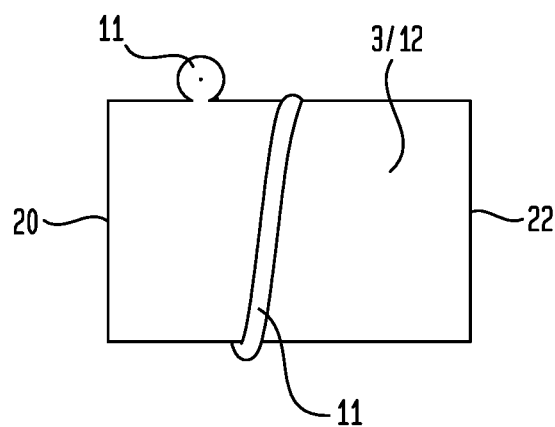
FIG. 12B is a side view of the release element of the connector system shown in FIG. 12A.
Figure 12C:
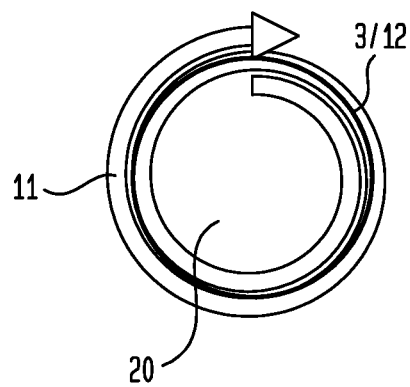
FIG. 12C is a first end view of the release element of the connector system shown in FIG. 12A.
Figure 12D:
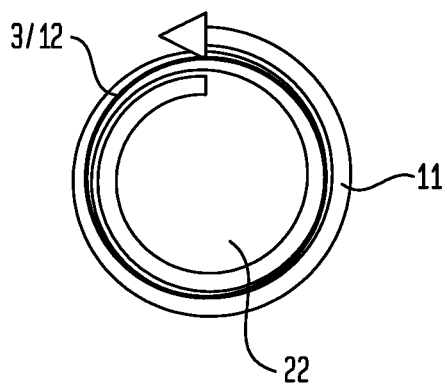
FIG. 12D is a second end view of the release element of the connector system shown in FIG. 12A.
Figure 14C:
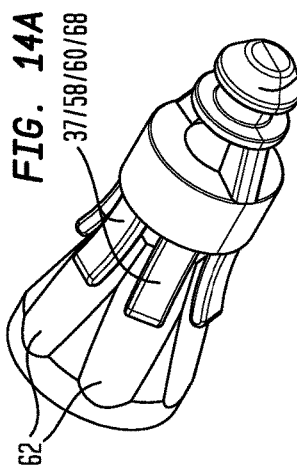
FIG. 14C is a top view of the particular embodiment of the valve-biasing member shown in FIG. 14A.
Figure 14B:
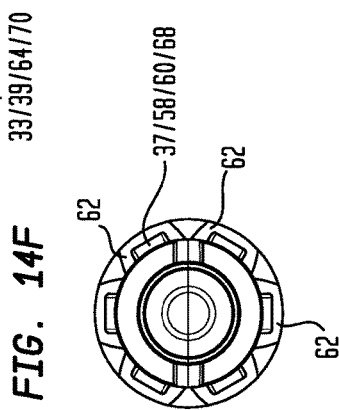
FIG. 14B is a side view of the particular embodiment of the valve-biasing member shown in FIG. 14A.
Figure 14A:
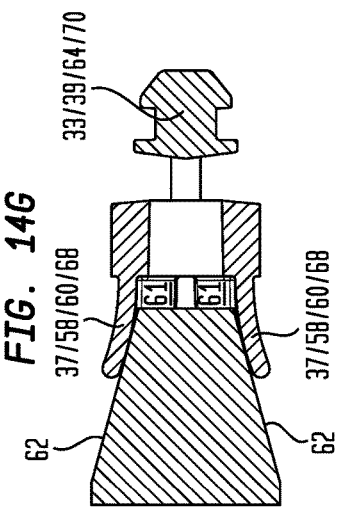
FIG. 14A is a perspective view of a particular embodiment of a valve-biasing member configured as a resiliently flexible member disposed in axially-adjacent relation to an angled surface, whereby the resiliently flexible member is in a flexed condition.
Figure 14F:
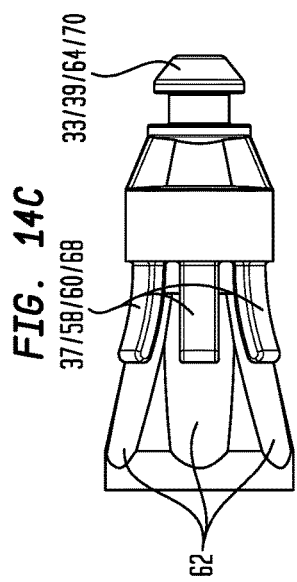
FIG. 14F is a second end view of the particular embodiment of the valve-biasing member shown in FIG. 14A.
Figure 14D:
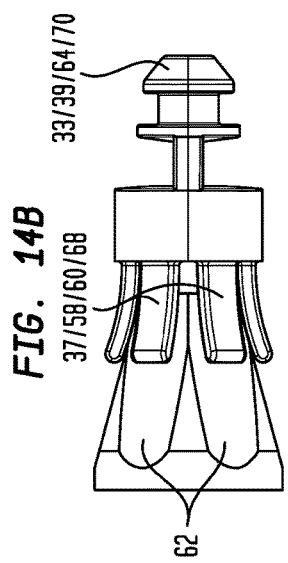
FIG. 14D is a bottom view of the particular embodiment of the valve-biasing member shown in FIG. 14A.
Figure 14G:
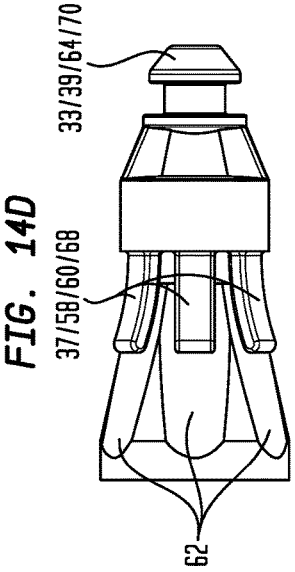
FIG. 14G is a cross-sectional view of the particular embodiment of the valve-biasing member shown in FIG. 14E.
Figure 14E:
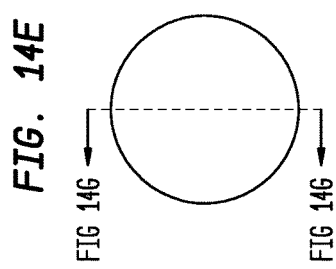
FIG. 14E is a first end view of the particular embodiment of the valve-biasing member shown in FIG. 14A.

When in a non-flexed condition (59) (as shown in the examples of FIG. 13A through FIG. 13G), the resiliently flexible member (58) can bias the second valve (64) toward the second valve closed position (69) in which the second valve (64) sealably occludes the second port (66) (as shown in the example of FIG. 5H and FIG. 7G).

Upon forcible urging, the resiliently flexible member (58) can be flexed toward a flexed condition (60) (as shown in the examples of FIG. 14A through FIG. 14G), allowing the second valve (64) to travel within the second valve seat (65) toward the second valve open position (70) away from the second port (66), thereby permitting fluid flow through the second port (66) and accordingly, through the second passageway (6) to provide the second passageway open condition (71) (as shown in the example of FIG. 5G).

Now referring primarily to FIG. 5G, the resiliently flexible member (58) can be flexed toward the flexed condition (60) upon forcible urging resulting from connection of the female and male couplers (3)(5), thus allowing the second valve (64) to travel within the second valve seat (65) toward the second valve open position (70) away from the second port (66), thereby permitting fluid flow through the second port (66) and accordingly, through the second passageway (6) to provide the second passageway open condition (71). Further, upon achievement of the connected condition (7) of the connector system (1), the first passageway (4) of the female coupler (3) can fluidicly communicate with the second passageway (6) to provide the fluid flow path (8) through which fluid can flow between the connector system first and second ends (41)(42).

Now referring primarily to FIG. 13A through FIG. 14G, as to particular embodiments, the resiliently flexible member (58) can be configured as a plurality of resiliently flexible members (58) which dispose in circumferentially spaced-apart relation to define an internal space (61). Additionally, an angled surface (62) can be disposed in axially-adjacent relation to the plurality of resiliently flexible members (58).

Upon forcible urging resulting from connection of the female and male couplers (3)(5), the plurality of resiliently flexible members (58) move axially toward the angled surface (62), whereby the angled surface (62) can be received within the internal space (61) while forcibly urging the plurality of resiliently flexible members (58) to flex about the angled surface (62) toward the flexed condition (60) (as shown in the examples of FIG. 14A through FIG. 14G). Correspondingly, the second valve (64) travels within the second valve seat (65) toward the second valve open position (70) away from the second port (66), thereby permitting fluid flow through the second port (66) and accordingly, through the second passageway (6) to provide the second passageway open condition (71).

Upon uncoupling of the female and male couplers (3)(5), the plurality of resiliently flexible members (58) are biased toward the non-flexed condition (59) (as shown in the examples of FIG. 13A through FIG. 13G), biasing the second valve (64) toward the second valve closed position (69) in which the second valve (64) sealably occludes the second port (66).

Again referring primarily to FIG. 13A through FIG. 14G, as to particular embodiments, the resiliently flexible member (58) and the second valve (64) can be formed as a one-piece construct; however, the invention need not be so limited.

Tubing

Figure 15A:
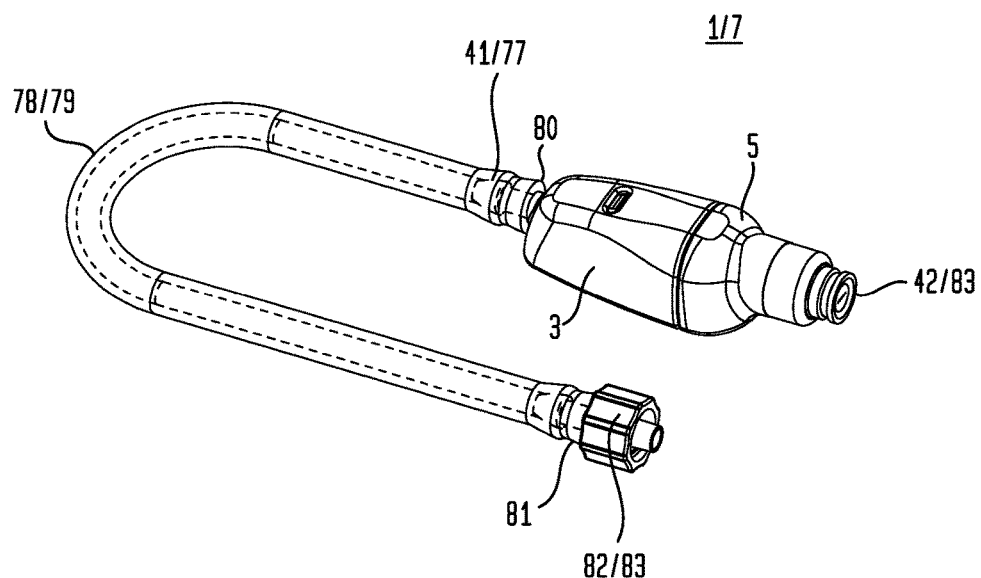
FIG. 15A is a perspective view of a particular embodiment of the connector system including a J-loop coupled to a connector system first end, whereby first and male couplers of the connector system are releasably matably engaged.
Figure 15B:
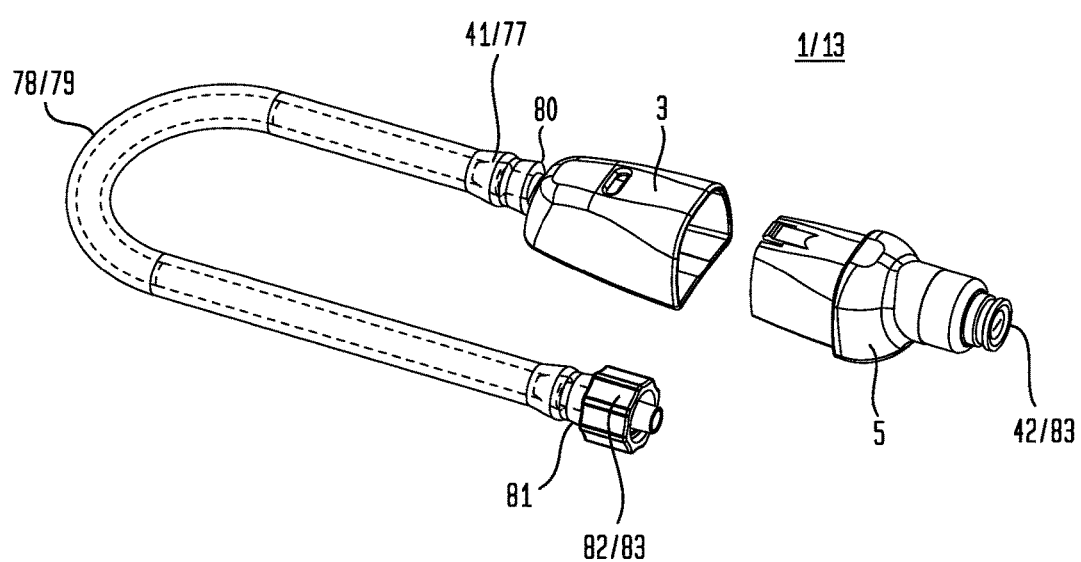
FIG. 15B is a perspective view of the particular embodiment of the connector system shown in FIG. 15A, but whereby the first and male couplers are in adjacent axial relation but are not releasably matably engaged.

Now referring primarily to FIG. 15A and FIG. 15B, as to particular embodiments, the connector system (1), as described above, can further include at least one tube (2) coupled to a connector system end (41)(42), for example the connector system first end (41), which can be configured as a barb (77). Accordingly, the tube (2) can engage with the barb (77), for example via frictional engagement about the barb (77), to securely couple the tube (2) to the connector system (1).

Again referring primarily to FIG. 15A and FIG. 15B, as to particular embodiments, the tube (2) can be configured as extension tubing (78), for example flexible extension tubing (78) such as a J-loop (79), having opposing J-loop first and second ends (80)(81), whereby the J-loop first end (81) can engage with the barb (77) outwardly extending from the connector system first end (41) to securely couple the J-loop (79) to the connector system (1), and the J-loop second end (81) can be configured to couple to an intravenous (IV) catheter, for example via an IV catheter connector (82) such as a luer lock fitting (83).

Again referring primarily to FIG. 15A and FIG. 15B, as to particular embodiments, the connector system second end (42) can also be configured as a luer lock fitting (83), which may be useful for connecting the connector system (1), J-loop (79), and IV catheter to a reservoir, whereby as but one illustrative example, the reservoir may contain fluids for intravenous delivery.

As to particular embodiments, the J-loop (79) can be configured to automatically disengage from the connector assembly (1) when a load force exceeds a predetermined threshold for safety.

A method of making a particular embodiment of a connector system (1) for releasably connecting tubes (2) can include providing a female coupler (3) having a first passageway (4), providing a male coupler (5) having a second passageway (6), movably coupling a catch (9) to the female coupler (3), coupling a catch-receiving element (10) to the male coupler (5), and movably coupling a release element (11) to the female coupler (3); wherein travel of the release element (11) along a female coupler outer surface (12) of the female coupler (3) disengages the catch (9) from the catch-receiving element (10) to achieve a disconnected condition (13) of the connector system (1).

A method of making another embodiment of a connector system (1) for releasably connecting tubes (2) can include providing a female coupler (3) comprising a first conduit (32) defining a first passageway (4), a first valve (33) operable to interrupt fluid flow through the first passageway (4), and a first valve-biasing member (37) disposed outside of the first passageway (4), whereby the first valve-biasing member (37) can be operable to bias the first valve (32) toward a first valve closed position (3); and providing a male coupler (5) comprising a second conduit (63) defining a second passageway (6).

The method of making the connector system (1) can further include providing additional components of the connector system (1) as described above and in the claims.

Components of the connector system (1) can be formed from one or more of any of a numerous and wide variety of materials capable of providing a functional connector system (1). By way of non-limiting example, the material can include or consist of: rubber, rubber-like material, plastic, plastic-like material, acrylic, polyamide, polyester, polypropylene, polyethylene, polyvinyl chloride-based materials, silicone-based materials, or the like, or combinations thereof. Additional non-limiting examples can include polymeric materials or resins, for example thermoplastics, such as acrylic, nylon, polybenzimidazole, polyethylene, polypropylene, polystyrene, polyvinyl chloride, polytetrafluoroethylene, or the like, or combinations thereof; thermosets, such as polyester fiberglass, polyurethanes, rubber, polyoxybenzylmethylenglycolanhydride, urea-formaldehyde foam, melamine resin, epoxy resin, polyimides, cynate esters, polycyanurates, polyester resin, or the like, or combinations thereof; elastomers, such as natural polyisoprene, synthetic polyisoprene, polybutadiene, chloropene rubber, butyl rubber, styrene-butadiene rubber, nitrile rubber, ethylene propylene rubber, epichlorohydrin rubber, polyacrylic rubber, silicone rubber, fluorosilicone rubber, fluoroelastomers, perfluoroelastomers, polyether block amides, chlorosulfonated polyethylene, ethylene-vinyl acetate, thermal plastic elastomer (TPE), or the like, or combinations thereof.

As to particular embodiments, one or more components of the connector system (1) can be formed from an antibacterial material(s).

As to particular embodiments, one or more components of the connector system (1) can be formed entirety from non-metallic material(s).

Additionally, components of the connector system (1) can be produced from any of a wide variety of processes depending upon the application, such as press molding, injection molding, fabrication, machining, printing, additive printing, or the like, or combinations thereof, as one piece or assembled from a plurality of pieces into a component of the connector system (1).

As to particular embodiments, one or more components of the connector system (1) can be disposable or reusable, depending upon the application.

A method of using a particular embodiment of a connector system (1) for releasably connecting tubes (2) can include obtaining the connector system (1) comprising: a female coupler (3) having a first passageway (4), a male coupler (5) having a second passageway (6), a catch (9) movably coupled to the female coupler (3), a catch-receiving element (10) coupled to the male coupler (5), whereby upon releasable matable axial coupling of the female and male couplers (3)(5), the catch (9) engages with the catch-receiving element (10) to fix an axial position of the female coupler (3) in relation to the male coupler (5), thereby achieving a connected condition (7) of the connector system (1) in which the first and second passageways (4)(6) dispose in fluidic communication to provide a fluid flow path (8), and a release element (11) movably coupled to the female coupler (3), whereby travel of the release element (11) along a female coupler outer surface (12) of the female coupler (3) disengages the catch (9) from the catch-receiving element (10) to achieve a disconnected condition (13) of the connector system (1); coupling a first tube (2) to the female coupler (3); coupling a second tube (2) to the male coupler (5); and releasably coupling the female and male couplers (3)(5) to achieve the connected condition (7) of the connector system (1).

As to particular embodiments, the method can further include flowing fluid through the fluid flow path (8).

As to particular embodiments, the method can further include forcibly urging the release element (11) to travel along the female coupler outer surface (12) to disengage the catch (9) from the catch-receiving element (10) to achieve the disconnected condition (13) of the connector system (1).

A method of using another particular embodiment of a connector system (1) for releasably connecting tubes (2) can include obtaining the connector system (1) comprising a female coupler (3) including a first conduit (32) defining a first passageway (4), a first valve (33) operable to interrupt fluid flow through the first passageway (4); and a first valve-biasing member (37) disposed outside of the first passageway (4), whereby the first valve-biasing member (37) can be operable to bias the first valve (33) toward a first valve closed position (38), and a male coupler (5) including a second conduit (63) defining a second passageway (6), whereby upon releasable matable axial coupling of the female and male couplers (3)(5), a connected condition (7) of the connector system (1) can be achieved, and whereby in the connected condition (13), the first valve (33) is forcibly urged toward a first valve open position (39) to allow fluid to flow through the first passageway (4); coupling a first tube (2) to the female coupler (3); coupling a second tube (2) to the male coupler (5); and releasably coupling the female and male couplers (3)(5) to achieve the connected condition of the connector system (1).

As to particular embodiments, the method can further include flowing fluid through the first passageway (4).

As can be easily understood from the foregoing, the basic concepts of the present invention may be embodied in a variety of ways. The invention involves numerous and varied embodiments of a connector system and methods for making and using such a connector system, including the best mode.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "connector" should be understood to encompass disclosure of the act of "connecting"—whether explicitly discussed or not—and, conversely, were there effectively disclosure of the act of "connecting", such a disclosure should be understood to encompass disclosure of a "connector" and even a "means for connecting". Such alternative terms for each element or step are to be understood to be explicitly included in the description.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment. The term "about" generally refers to a range of numeric values that one of skill in the art would consider equivalent to the recited numeric value or having the same function or result. Similarly, the antecedent "substantially" means largely, but not wholly, the same form, manner or degree and the particular element will have a range of configurations as a person of ordinary skill in the art would consider as having the same function or result. When a particular element is expressed as an approximation by use of the antecedent "substantially," it will be understood that the particular element forms another embodiment.

Moreover, for the purposes of the present invention, the term "a" or "an" entity refers to one or more of that entity unless otherwise limited. As such, the terms "a" or "an", "one or more" and "at least one" can be used interchangeably herein.

Further, for the purposes of the present invention, the term "coupled" or derivatives thereof can mean indirectly coupled, coupled, directly coupled, connected, directly connected, or integrated with, depending upon the embodiment.

Thus, the applicant(s) should be understood to claim at least: i) each of the connector systems herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application, if any, provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

Additionally, the claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

The invention claimed is:

1. A connector system for releasably connecting tubes, comprising:
    a female coupler comprising:
        a first conduit defining a first passageway;
        a first valve operable to interrupt fluid flow through said first passageway;
        a fluid-tight seal between a first valve inner surface of said first valve and a first conduit outer surface of said first conduit; and
        a first valve-biasing member disposed outside of said first passageway, said first valve-biasing member operable to bias said first valve toward a first valve closed position; and
    a male coupler comprising:
        a second conduit defining a second passageway, said second conduit capable of longitudinal travel within said male coupler;
        a second conduit-biasing member disposed outside of said second passageway, said second conduit-biasing member operable to bias said second conduit to provide a second passageway closed condition;
    wherein upon releasable matable axial coupling of said female and male couplers, a connected condition of said connector system is achieved; and
    wherein in said connected condition, said first valve is forcibly urged toward a first valve open position to allow fluid to flow through said first passageway and said second conduit is forcibly urged to provide a second passageway open condition to allow said fluid to flow through said second passageway; and
    wherein in said connected condition, said first passageway fluidicly communicates with said second passageway to provide a fluid flow path through which said fluid can flow between connector system first and second ends.

2. The connector system of claim 1, wherein said first valve telescopingly disposes about said first conduit.

3. The connector system of claim 2, wherein said first valve is capable of longitudinal travel over said first conduit.

4. The connector system of claim 3, wherein said first valve inner surface disposes adjacent said first conduit outer surface.

5. The connector system of claim 1, wherein a portion of said first conduit outer surface provides a first valve seat in which said first valve is movable.

6. The connector system of claim 5, further comprising a first seal assembly fixedly coupled to said first conduit in axially spaced apart relation;
    wherein sealable engagement of said first valve with said first seal assembly provides said first valve closed position.

7. The connector system of claim 6, further comprising a second seal assembly fixedly coupled to said second conduit in axially spaced apart relation;
    wherein sealable engagement of said second seal assembly with an engagement surface provided by said second valve seat inner surface provides said second valve closed position.

8. The connector system of claim 7, wherein a second valve-biasing member biases said second seal assembly toward said engagement surface.

9. The connector system of claim 8, wherein said second valve-biasing member comprises a resiliently compressible member.

10. The connector system of claim 9, wherein said resiliently compressible member comprises a spring.

11. The connector system of claim 1, wherein a second valve is provided by said second conduit.

12. The connector system of claim 1, wherein said second valve-biasing member disposes radially outwardly from said second valve.

13. A connector system for releasably connecting tubes, comprising:
    a female coupler comprising:
        a first conduit defining a first passageway;
        a first valve operable to interrupt fluid flow through said first passageway;
        a fluid-tight seal between a first valve inner surface of said first valve and a first conduit outer surface of said first conduit; and
        a first valve-biasing member disposed outside of said first passageway, said first valve-biasing member operable to bias said first valve toward a first valve closed position; and a male coupler comprising:
a second conduit defining a second passageway; and
a second valve operable to interrupt fluid flow through said second passageway;
wherein said second conduit and said second valve are formed as a one-piece construct; and
a second valve-biasing member disposed outside of said second passageway, said second valve-biasing member operable to bias said second valve toward a second valve closed position;
wherein upon releasable matable axial coupling of said female and male couplers, a connected condition of said connector system is achieved; and
wherein in said connected condition, said first valve is forcibly urged toward a first valve open position to allow fluid to flow through said first passageway and said second valve is forcibly urged toward a second valve open position to allow said fluid to flow through said second passageway; and
wherein in said connected condition, said first passageway fluidicly communicates with said second passageway to provide a fluid flow path through which said fluid can flow between connector system first and second ends.

14. A connector system for releasably connecting tubes, comprising:
a female coupler comprising:
a first conduit defining a first passageway;
a first valve operable to interrupt fluid flow through said first passageway;
a fluid-tight seal between a first valve inner surface of said first valve and a first conduit outer surface of said first conduit; and
a first valve-biasing member disposed outside of said first passageway, said first valve-biasing member operable to bias said first valve toward a first valve closed position; and
a male coupler comprising:
a second conduit defining a second passageway; and
a second valve operable to interrupt fluid flow through said second passageway;
wherein said second valve is fixedly coupled to said second conduit;
a second valve-biasing member disposed outside of said second passageway, said second valve-biasing member operable to bias said second valve toward a second valve closed position;
wherein upon releasable matable axial coupling of said female and male couplers, a connected condition of said connector system is achieved; and
wherein in said connected condition, said first valve is forcibly urged toward a first valve open position to allow fluid to flow through said first passageway and said second valve is forcibly urged toward a second valve open position to allow said fluid to flow through said second passageway; and
wherein in said connected condition, said first passageway fluidicly communicates with said second passageway to provide a fluid flow path through which said fluid can flow between connector system first and second ends.

15. The connector system of claim 14, wherein a portion of said first conduit outer surface provides a first valve seat in which said first valve is movable.

16. A connector system for releasably connecting tubes, comprising:
a female coupler comprising:
a first conduit defining a first passageway;
a first valve operable to interrupt fluid flow through said first passageway;
a fluid-tight seal between a first valve inner surface of said first valve and a first conduit outer surface of said first conduit; and
a first valve-biasing member disposed outside of said first passageway, said first valve-biasing member operable to bias said first valve toward a first valve closed position; and
a male coupler comprising:
a second conduit defining a second passageway;
a second conduit-biasing member disposed (i) about said second conduit and (ii) outside of said second passageway, said second conduit-biasing member operable to bias said second conduit to provide a second passageway closed condition;
wherein upon releasable matable axial coupling of said female and male couplers, a connected condition of said connector system is achieved; and
wherein in said connected condition, said first valve is forcibly urged toward a first valve open position to allow fluid to flow through said first passageway and said second conduit is forcibly urged to provide a second passageway open condition to allow said fluid to flow through said second passageway; and
wherein in said connected condition, said first passageway fluidicly communicates with said second passageway to provide a fluid flow path through which said fluid can flow between connector system first and second ends.

17. The connector system of claim 16, wherein said first valve-biasing member biases said first valve toward a first seal assembly.

18. The connector system of claim 17, wherein said first valve-biasing member comprises a resiliently compressible member.

19. The connector system of claim 18, wherein said resiliently compressible member comprises a spring.

* * * * *